United States Patent
Marshall et al.

(10) Patent No.: US 9,339,526 B2
(45) Date of Patent: May 17, 2016

(54) METHODS FOR TREATING DISORDERS THAT INVOLVE IMMUNOGLOBULIN A

(75) Inventors: Aaron Marshall, Winnipeg (CA); Sen Hou, Winnipeg (CA)

(73) Assignee: UNIVERSITY OF MANITOBA, Winnipeg, Manitoba (CA)

( * ) Notice: Subject to any disclaimer, the term of this patent is extended or adjusted under 35 U.S.C. 154(b) by 0 days.

(21) Appl. No.: 13/979,887

(22) PCT Filed: Jan. 17, 2012

(86) PCT No.: PCT/IB2012/000053
§ 371 (c)(1),
(2), (4) Date: Aug. 9, 2013

(87) PCT Pub. No.: WO2012/098449
PCT Pub. Date: Jul. 26, 2012

(65) Prior Publication Data
US 2013/0318644 A1 Nov. 28, 2013

Related U.S. Application Data

(60) Provisional application No. 61/433,449, filed on Jan. 17, 2011.

(51) Int. Cl.
*A61K 38/17* (2006.01)
*G01N 33/50* (2006.01)
*G01N 33/68* (2006.01)
*A01K 67/027* (2006.01)

(52) U.S. Cl.
CPC ......... *A61K 38/1709* (2013.01); *A01K 67/0276* (2013.01); *G01N 33/5088* (2013.01); *G01N 33/6854* (2013.01); *A01K 2217/075* (2013.01); *A01K 2227/105* (2013.01); *A01K 2267/0387* (2013.01); *G01N 2333/4721* (2013.01); *G01N 2500/10* (2013.01); *G01N 2800/18* (2013.01)

(58) Field of Classification Search
CPC ....................... A61K 38/1709; G01N 33/5086
See application file for complete search history.

(56) References Cited

U.S. PATENT DOCUMENTS

| | | | |
|---|---|---|---|
| 4,703,004 A | 10/1987 | Hopp et al. | |
| 4,782,137 A | 11/1988 | Hopp et al. | |
| 5,139,932 A | 8/1992 | Cederholm et al. | |
| 5,594,115 A | 1/1997 | Sharma | |
| 5,935,824 A | 8/1999 | Sgarlato | |
| 7,514,594 B2 | 4/2009 | Askew et al. | |
| 7,663,017 B2 | 2/2010 | Lone et al. | |
| 7,705,198 B2 | 4/2010 | Lewis et al. | |
| 8,053,627 B2 | 11/2011 | Popko et al. | |
| 2006/0280744 A1 | 12/2006 | Popko et al. | |
| 2008/0124344 A1* | 5/2008 | Combs et al. | 424/172.1 |
| 2009/0029908 A1 | 1/2009 | Mukherjee et al. | |
| 2010/0281548 A1 | 11/2010 | Popko et al. | |
| 2011/0173708 A1 | 7/2011 | Combs et al. | |

FOREIGN PATENT DOCUMENTS

| | | | |
|---|---|---|---|
| JP | 2000/295991 A | 10/2000 | |
| WO | 2006/113958 A2 | 11/2006 | |
| WO | WO2006/113958 | * 11/2006 | ................ A23J 1/00 |
| WO | 2012/098449 | 7/2012 | |

OTHER PUBLICATIONS

Hou et al. (Mucosal Immunol. 2014).*
Roberts et al. (Cancer 1975: 36:221-224).*
Al-Alwan et al. "Follicular Dendritic Cell Secreted Protein (FDC_SP) Regulates Germinal Center and Antibody Responses" 2007. *J. Immunol.* 178(12):7859-7867.
Bowie et al. "Deciphering the Message in Protein Sequences: Tolerance to Amino Acid Substitutions". 1990. *Science.* 247:1306-1310.
Branda et al. "Talking About a Revolution: The Impact of Site-Specific Recombinases on Genetic Analyses in Mice" 2004. *Dev. Cell.* 6:7-28.
Evans et al. "Establishment in Culture of Pluripotential Cells from Mouse Embryos". 1981. *Nature.* 292:154-156.
GenBank Accession No. AAN01116. "Follicular Dendritic Cell Secreted Peptide Precursor [*Homo sapiens*]". National Center for Biotechnology Information. Retrieved from the Internet on May 2, 2014. Retrieved from the Internet at https://www.ncbi.nlm.nih.gov/protein/AAN0116. 1 page.
GenBank Accession No. AF435080. "*Homo sapiens* Follicular Dendritic Cell Secreted Peptide Precursor, mRNA, Complete Cds". National Center for Biotechnology Information. Retrieved from the Internet on May 2, 2014. Retrieved from the Internet at https://www.ncbi.nlm.nih.gov/nuccore/AF435080. 2 pages.
GenBank Accession No. BC037156. "*Mus musculus* cDNA Sequence BC037156, mRNA (cDNA Clone IMAGE:4168546)". National Center for Biotechnology Information. Retrieved from the Internet on May 2, 2014. Retrieved from the Internet at HTTPS://WWW.NCBI.NLM.NIH.GOV/NUCCORE/bc037156. 2 pages.
GenBank Accession No. BAD77806.1. "Follicular Dendritic Cell Secreted Peptide [*Rattus norvegicus*]". National Center for Biotechnology Information. Retrieved from the Internet on May 2, 2014. Retrieved from the Internet at https://www.ncbi.nlm.gov/protein/BAD77806.1. 1 page.
GenBank Accession No. XP_001160925. PREDICTED: follicular dendritic cell secreted peptide [*Pan troglodytes*]. National Center for Biotechnology Information. Retrieved from the Internet on May 2, 2014. Retrieved from the Internet at https://www.ncbi.nlm.nih.gov/protein/XP_0011602925. 1 page.
Harlow et al. 1988. Antibodies: A Laboratory Manual. Cold Spring Harbor Laboratory Press, Cold Spring Harbor.

(Continued)

*Primary Examiner* — Scott Long
(74) *Attorney, Agent, or Firm* — Mueting, Raasch & Gebhardt, P.A.

(57) ABSTRACT

Provided herein are FDC-SP polypeptides and methods of using such polypeptides. Methods include, but are not limited to, altering IgA concentration in a subject, treating a subject having signs of a disorder that includes excessive IgA production, identifying a compound that decreases the concentration of IgA in an animal, and identifying a compound that treats a condition associated with increased levels of IgA. Also provided herein is an animal that has decreased expression of an endogenous FDC-SP coding sequence. The animal may develop pathophysiological features of IgA nephropathy, and/or may display increased IgA in serum, saliva, bronchoalveolar lavage fluid, or a combination thereof; increased IgA expressing B lymphocytes in circulation, lymphoid tissue, or a combination thereof; or increased IgA production in vitro by isolated B lymphocytes.

19 Claims, 22 Drawing Sheets

(56) References Cited

OTHER PUBLICATIONS

Li et al. "Identification and Characterization of a Novel Nasopharyngeal Carcinoma-Associated Peptide: NAP-I" 2004. *J. Trans.Med*. 8 pages.

Marshall et al. "FDC-SP, A Novel Secreted Protein Expressed by Follicular Dendritic Cells" 2002. *J. Immunol*. 169:2381-2389.

Marshall. "Follicular Dendritic Cell Secreted Peptide (FDC-SP) is a Novel Chemotactic Factor Specific for B Cells Activated by T-Dependant Signals" 2004. Fed. Of American Societies for Experimental Biology, Annual Meeting. 774.1-Abstracts of Papers. 1 page.

Nakamura et al. "Identification of Genes Preferentially Expressed in Periodontal Ligament: Specific Expression of a Novel Secreted Protein, FDC-SP" 2005. *Biochem Biophys Res Commun*. 338:1197-1203.

Orban et al. "Tissue- and Site-Specific DNA Recombination in Transgenic Mice". 1992. *Proc. Nat. Acad. Sci. USA*. 89:6861-6865.

Robertson, E.J., In: Current Communications in Molecular Biology, Capecchi, M.R. (ed). Cold Spring Harbor Press, Cold Spring Harbory, NY. 1989. pp. 39-44.

Shinomura et al. "Adsorption of Follicular Dendritic Cell-secreted Protein (FDC-SP) into Mineral Deposits: Application of a New Stable Gene Expression System" 2008. Journ. Of Bio.Chemistry. 283(48):33658-33664.

Tatusova et al. "BLAST 2 Sequences, A New Tool for Comparing Protein and Nucleotide Sequences" 1999. *FEMS Microbiol Lett*. 174:247-250.

Wang et al. "C4orf7 Contributes to Ovarian Cancer Metastasis by Promoting Cancer Cell Migration and Invasion". Oncol. Rep. 2010. 24:933-999.

Supplementary European Search Report for related Application No. PCT/IB2012/000053. Issued May 19, 2014 by the European Patent Office. 9 pages total.

Machine Translation of Japanese Patent JP2000/295991A provided by the Japanese Patent Office on Jul. 3, 2014. 100 pages.

* cited by examiner

Figure 1A

```
mFDC-SP     1:..MKTLLLAAIVAVTACLPVPKDQEREKRSASDSDSDEFPLRIPFPPYGLPFGTYPPFLN:59
rFDC-SP     1:..MKALILESAIIATTACLPVPEDQEREKRSAS....DETPERISFPPGPPFGGYPPFFN:55
hFDC-SP     1:MKKVLILAIITAIEAVGFPPVSQDQEREKRSISDS...DELASGFFVFYPYPFRPLPPIPF:58
cFDC-SP     1:MKKVLLLTAIIAIEAVAAGFPPVSQDQEREKRSISDS...DELASGFFVFYPYPFRPLPPIPF:58
consensus   1:--.-!!--**!*!--!!!!!!!!!!!!!!!!!---.**!!!*--*!*!-!!----:60 mFDC-SP    60:QGLPWYYYYVP.PFFLPFLPPLADP...:84
rFDC-SP    56:QGNPWYYYYYNPFLVPIIPPTRTP...:81
hFDC-SP    59:PREPWFRRNFP..IPIPESAPTTPLPSEK:85
cFDC-SP    59:PREPWFRRNFP..IPIPESAPHTPLPSEK:85
consensus  61:--*!!-****!!--*!*!!-*!*!*!---:89
```

Figure 1B

```
SEQ ID NO:10
ATTTCTCATAACAGCGTCAGAGAGAAAGAACTGACTGAAACGTTTGAGATGAAGAAAGTTCTCCTCCTGA
TCACAGCCATCTTGGCAGTGGCTGTTGGTTTCCCAGTCTCTCAAGACCAGGAACGAGAAAAAAGAAGTAT
CAGTGACAGCGATGAATTAGCTTCAGGGTTTTTTGTGTTCCCTTACCCATATCCATTTCGCCCACTTCCA
CCAATTCCATTTCCAAGATTTCCATGGTTTAGACGTAATTTTCCTATTCCAATACCTGAATCTGCCCCTA
CAACTCCCCTTCCTAGCGAAAAGTAAACAAGAAGGAAAAGTCACGATAAACCTGGTCACCTGAAATTGAA
ATTGAGCCACTTCCTTGAAGAATCAAAATTCCTGTTAATAAAAGAAAAACAAATGTAATTGAAATAGCAC
ACAGCACTCTCTAGTCAATATCT
```

Figure 2B-01

```
AAATGGGGCTTGGCCATGATGTGTGGTTGATATACTTAGCGTCACTCCATTGGACAAAA
CTGATTATCCGTTGATAACAGCAGTTTTGGTTATAAATAGTTTCTTGATTAGGGGTGGA
ACTTTGTGTCCACATCCTCTTCCCTCCATCTTGGGACTTTGTCTTGTTTGAGTAGGAAG
TTGGGTGGGTAGGGAGGTATTTGAGATCTAGAAGAAGTTGGGCAAAGGGAAAAAATATG
ATGAAAATACATTGTATGAAAAATGTAATGGTGGTAAAGGTACCCATGTGGAAAAAAA
AAAGAAAAGAAGAAATAAAGTAGGTAGAAGACTTGTTGAGAAGGATTTCAGTGGGA
GAGAGAATGAAAGCAGGCAACGAAGGCTGAAGTGGTAAAAAAATATCATCATATACAC
ACAGAAAACTATAAAACGAAAATGAAAAATGTGGTGGACTCATGTGTGTTGGTTGAC
TGTCCGTCCAACATCATAGTGAATTATGCAGCTGGATAAAAGAACCTGTGCACCAGAA
GATCTTAGATAAGCCATGGTCTCAGAGTAGGGACTGATTACATACCCTACTCATTAGAA
GTGAGGACAAAAGCCATATGTGGTCAAGTGCATACAGTAAATTCAAGGGGGAATCAGAA
CACACAAGGCTTCTGAGGAaggaggaggaggaggaggaggaggaggaggaggaggagga
ggagaagaaggaggaagtggagTTCTGAGAGAATTTTTACATAACAGGACAATGGATGG
GTAGGTAGGGAGAATCTGGAAGGAGCTAGGGGAGGAGAGAGAATGTGATACaaatatat
tatatgaaaaataaaataatttaaGGGAACCACAGGAAAGAAATAATAGAACTTTGtt
attttaattaaaaaatcattattaaatGTCAAGACATAAAATTTCATGAAGATAGAAAG
TATATCTGGGCCTCAAAAATAAGTGACAACTAGCAATTTTTACTAGAATACTTTCAGCT
AAGTAAAAGAAACTAAAATCAACTTTTAGGAAAGGCATTCAGAAACATGCCATACAaca
cacacacatacacgtatgggtactcatgcatacacacacacacacacacacacacacac
atgcacTTAACAAGTCTACCTCTGAATGAGAACCTACTCTTACCTCAGAATGATCAAAA
TGAAAACTAATATATGTTGATATATTGTATTTAACAGATCATCAGTTCAGTTCTCTTAA
AGCCAGTGAAACAAGAATAAATGTTGTTATGTATAATAAACTTTAGTGTTTCTTTGGAT
TTCTCTACCCTTCGAGTGGCACTGTAAAATGCTGGTTATAGATGGGTCTTGGAAACCAA
TTGCAGAAATCAACATAATATTGACAGAATTCTAGTTGTGGTATTTAAATCAAGTGCT
AACTCTCTCAATTTCTCAGGCCATTGGCGTACACTGGCGTAAGATCTAATAATCATTTT
GCACTTGCTGCTGGCTGTTCTAGAGATTAAGTGGAATAATAGACACGCAACACTTTTGT
CTATAGAGCAATAAGCCCCAAATCCATGAGAGACAAATTTAAAGGAAAACCACAAAGG
AAATATTCTGTATCACTCAACCATAGTTTCTATGAAACTACCAGTATCACTCATTTCTC
AGTTTCAATGGATTATGGTAGTTGAGTCAGTAGAATACTGACTGATCCCAGGAGCAGCT
TTCCAGCCAAGGACTTCTCCATTCCATTGTGCTGGGAGTGTATAAAAGAGATGCAACAG
TGAGGTGCCTGTCATCTTCCCTGACGATAGCAGTATCAGCTAGAAGGAGCAGAGTGGA
GAGTTTCAGGTAAGAAGGCTCTGAACTAATGCTGTAAACTATGGATATCAACTCTTCT
AGGAGACAGATGGTATATGTACATATTAATTTTTTCAAACTACCAGAATTGAAACTGTA
ATGGGACACTTGCTTGAAATTACAAACAGTGATTTGACTGTCCACTTGTGTATTTCTGT
TTGTATAAATTTAAAACCACCATTTTTCTATAGTAAGGATTTAAGAATGACCATAAAGG
AATCTTTGCAAGGACTGGGCACTGACGAGAGGAATGGAAATAGCATCAGGTTCATAATT
TTGAATTTTATGGACCAAGTCAACAAATATGGAAGGAATTCTATGGGTATGAAGAATTA
ACCTTCCATGCAGTGGTGCAAATCTTTAGTGACAGCATTTGGGAGGCAAGGCCAGTGAA
TGTATCTCTGTAAGTTTGAGGCCAACCTCGTCTATCCAGTGAGTTCCAGGACGGCCAGA
GCTACACAGTGAGTCTCTGTCTTGGCCGGGAAAAAGAATTAGGACTTTGTTAGTAACA
TCCTGTTCATCTTTAAAGTATCATCATTTATGCACCATTCTAATATGTCATATTGATTT
CAAATAATAATTATTTAAATTCTCTTTATATCAACCTTTGAATGAAATTGGTGGTGCC
ACAAAACACATCTGATGCATAAGACTTttcttttttaggttctctttctttgcatgtt
tattatttgtgtaaagaaaagttactgatttgtgagagttgagtctgtatcatgctaca
ttgctgaatttgtttatcatttctaaaagtttcacagtagaattttgggttctcttatg
```

Figure 2B-02

```
tatGTAACAATATACTACTAGGGCTTGGGGGGAAAACGGTCATTGGTAATTATGGCATA
TAGCAATTATAAAACAAAGGAGTCTGTGATGTGTTTTCTGTTTAATGAGATTTTAAATA
ATCCTTGAAAACTATTCCTTTGTATAAAATTCTCTACAATTCTATTCTCTTCAAGACTT
ATTTCCCCATTCTGTCTCTTCTATATTCTCTCCATATTTTGTAACTTCTGCCCATAGTA
TATATCACATATTGTTTTACATTACAAAGACATAATTATCTATCTCTGAGTAGTCTCCA
CCTGAAAGGGCTCAAGCTTTATAGTTATATCCTTGAGAGTGGCCTGCACAATGTCTGAA
GAAGGAAGGTAGAAGTGTATAAAATGAGGGACACATTGTACTATCGGTTTTCTATACTG
AGAGTTGGCCATTAGAATGCTAAACCTGACAAAACTTTTAAATACATGTCTTTAAACTC
ATCAATTACATCCCAGTATGCTGTATATTCTAGTAACATTTTCATTGATATGATGAGAA
AGAAACAAAGACAGAGTTCAAGATGTAGCAACATTTTATTCTTTTATGTTT
                              (SC3-416)
TACTCTTCTGTCTCATAGAAAAGGGATAAAGTGATAAAAACGAATAGCCATGATCTCAA
AGTTGTCCACAAATGATGTTAGTGAAATGGGAAATGAGCATTTTTCTCAGTGTAAAATA
ATAAATATTCTTCAGAAAACTGTAGTTCATACTGACCACTAACTCTCTAGTTAATAAGG
CTTTTAAGACAGTATTCATAAATATGTGAATACTTATTTTTAAAGAACTGATACAATGA
AGTCATAAAAACACAAACCATTCCAGTATTTACTTTTGAAAAGTTTCCCACTAGTAAAC
AGGCAATAAACTGCccctatgctactccgtcataacttcgtatagca
      (LoxP site)
tacattatacgaagttatcgctctcctgagtaggGCCCAAATGGCCAGCTAAGTCCTGA
GAACTATTAGTTACATACACTGTACCAGGCTTGCATCTTCTGGATTTC
                                  (Reverse of SC3-421)
CGTTAATAATCAGTTTTCTTTATGATGCCTAGAACAAGATGAAAACTCTTCTCCTGCTC
GCTGCCATCGTGGCAGTAACTGCTTGTCTCCCGTGAGTACTCACATCTAATCTCTAAA
GTGTTTATGAAGTTTAGATTCACGATTCTCGACAATGTTATTGCTCTTTCTTCACACTT
TAGTGTTTAAAGATACTTTCAACCTGACCTGTAGCATTATATTTCAGGAAATGTCATAT
GCTCTTTGGTGCATGACTGATGCCACGTAGTTTTTGTGCAGTAGCAAACACAATAACAT
TTAAAATTCTCTCTGAGAAATGGGAGCACCATCCAGTACTAGAGCACTTACCTGATAGC
TGTCTCAGTTTCTATTGTCGTGATAAACACCATAACCAAAACCAGCTTGGGGGGGGTTG
TTTTGTTGCACTTTGCAGCTTAGCTCTTAGGTCACATCCCATCACTAAAGGATGCCAGA
GCAGCAACTAAAGACAGGAACAGGAGACCAGAAACAAAGCTGAGGCTATGGAGAGGTGC
TGCTTGCCGATTTGCTCCCTGTGGCTTATTCATCATGCTTTCCCATACAACTTAGGGCC
ACCTGCTCAAGGATAGTGCTGACTGAGTGGCCTGGGTCCTTCCACACCAATAATTAAAG
AAGAAAATGCCCTATAGACTTGCCCAAGAGAAAACGGATGGAGACATCAGGTTCCCCTT
CCCAGAGAACCCAACTTTGTATCTGGTTGACAAAAACAAGCCTGGACACTAACTTTGAG
GACCCAAAGGATTCTCAAAGTATCAAAGGATGGTTGATCCTCAGCACCACAAAAAGAAA
AGGCAATCATGATGACCAGTAGCATTTTTTCCTGAATATTGCCTCTATATCTGGACAAC
CAAGTCCTATATTTTGATGGATAGCATGAAACAGTATTAGAAAGTAGTTGAATTATTTT
TTACATGTATATGCATATATTTCTCATGTGTTTACATCAGGACGAGTTAATTTCACTTA
TTGACTTTTAGGTGCCTAAGGACCAGGAACGAGAAAACGAAGTGTAAGTTGCTTTTCA
TCTTCCCATGTCAGTTTgtttgtgtgtgtgtctgtgtgtgtgtgtgtgtgt
tgtgtgtgtgtgtgtgtgtgtgtgtgtAAGATAGTCACAACTGTGATTAAAGGCA
TTTAGACACCCAAACCTCTTGACCTCTGAGAGAGTCTCAAAAATCTTTGGAATATTAGC
ATTAGACTAGTGTATAGAGTTTGATTTCGGGGAATACCTGAATTCAGTATAAATTAAT
TGGTTAATATCTGCCTATATAAAGAAAAAAACCTTTTCATTTCATATAAAAGTGACATG
CAGGTTTAGTTGTGTGTCACTCTGTGACAAAGGGCACAGTGCAGTTCTCACAGGGAACT
TCCTAAAATACCTCACCTCTTAAAGGCAACATTTTTCAATAGCATTGAGTTAGGGACCA
AGTGATCTATCTAAGCATAAATGATCTAAGAACATTTGACTTCCCATTCCAGGTGGTAG
```

Figure 2B-03

TAGGCCAGTCTTAATGACAAAAGTCGGAAAAAAAAAAACAGCAAAACATTATTTTGGTA
TGAACAGACAAGTAAAAACATTCAAGAAAAATGGGGCATGGGAATGAAGAAAGACAG
ACGTACTTACAGAAAAACTGGGATGAAGTAGGCCATGTGCTCTGATGGAAATGTACCTG
TGGCAGCCTCGAAATTCATCACTCTATTATATACAGCAGGAATGAGAAAGAAGTGAGTT
AGCTAATGTCAGCAGAAGGTCTCTGGATGGGAGTGGTTTTAGATAGCAGTCATTTGGGA
GGAGGAAGCACCAAATGCCGCTTTTGCACACACTGGTTTTAGCTAACTGTAACCATTTC
ATACATTGGCTAGGCGAAGACTTAAACGTTCTTCTGAGCCTAACCTTGATTTGCCATTC
CCTTTGGTCTAAGACATTGAAATCCTTGACCAGGCCATTCTTAGGTCAATAATATTGCA
CTCCACCCATGCAGCACAAAAACTGATAGAAATGTAGACACAGAATGAGAGGAAGAAAT
AAAGAGATGATTTTCAACATGTGATTTGGTTAATGGTCATATGAATCAAAACAATACAT
ATTACAGAGCCTTCACCTCTCTTATCATTCGTTGCCTTATAGCTATAGAAAGAATTATT
TGAAAAATTTGCTTTGAAGTCTAAGATTTGGAATGTAGTTATCTCTAATTTTCTAAACT
GAAATAATTAAGCCCTTGTTAATTTTACAAATAAAGACTGGCCTTTCCTTTTATCAACA
GGCCAGTGACAGTGACAGTGATGAATTCCCTTTACGGATTCCCTTTCCCCATACGGGT
ATCCATTTGGTACATACCCACCATTCTTAAATCAAGGCTACCCGTGGTATTATTATTAT
TATCCTCCTTTTCCCCTGCCCTTCACCCCCCCTCCAACTGCAGATCCTTAACTGCAAAT
GAAAGAAAAGTCACACTGTGGATTATTTAAGGTGAGTTTGAATAATCAGTCACTTTGGC
TGTTCTGTTTCTTATTTGTGAGTATAAACGCATCACTCCATGAAAATGTTACACTGTTG
CTAGCTATTAGGATCGTACATGTTTCCGTGGTTTTCTGCAGTAAATATTGTTGGTACCA
ACAGTGGAGTTATATACTATGTGTCCTTTTGATCCAATAACACAACAGTTTAAATTCCT
TGTTTGTTACAATACAATAAAACCAAGTCTGTTTTCATAATTTTATTTAAGCATTTTCT
ACTAAAACAGTTTTCCACTTTGGGATGAATCATAGGAATAGTAGAAGCAAATGTCAATA
TAAAGCTGAGCCTGTATGAACTTATGAATCTAGACAGTAAAGGAAAGTTTAAGGGTTAG
GTTCTTCCTAACCCTTAGGAAAGTAAGCTAAGATTTTTAATGTTAATCACCCAAAACAA
TGGTGTATGCCTAACATTAAAAAAAAAAAACCTATAGCCTTATGTTTCACTTAAAATA
TAGTTACTGTTATCTCAGCATACCAGACTCAAAGTGGTGAGTCTGCAAGCCCTGGATAG
ATTGGGTACAGGCTATATTGTAGACTAATTACAGACCCAAAACATTTTAGAAAACAAAA
ACTTCTCACTGTAATGCacatacatataatatgtgtacacaaacacatgcacacact
catacatgcacatatacacacatgtacacacatacacacatacatacatgcacacatac
atacatacatacatacatacatacatgtacacacacaCAGAAAGGCTCTGACTTT
TTCTTTTTCTATTCAGCATTCATGTGCTAAATGTTTTCCAAGTCTTGAGCTACATGGAT
TTTTATGACAACATATATCATAAGATACAATATACGTGTATACGTATAataacttcg
       (LoxP site)
tatagCatacattatacgaagttatGGATCCTGATATCCCTATGCTACTCCGTCgaagt
tcctattctctagaaagtataggaacttcattctaccgggtaggggaggcgcttttccc
aaggcagtctggagcatgcgctttagcagccccgctgggcacttggcgctacacaagtg
gcctctggctcgcacacattccacatccaccggtaggcgccaacc
                        (Reverse of 4R2)
ggctccgttctttggtggccccttcgcgccaccttctactcctcccctagtcaggaagt
tccccccgccccgcagctcgcgtcgtgcaggacgtgacaaatggaagtagcacgtctc
actagtctcgtgcagatggacagcaccgctgagcaatggaagcgggtaggcctttgggg
cagcggccaatagcagctttgctccttcgctttctgggctcagaggctgggaaggggtg
ggtccgggggcgggctcaggggcgggctcaggggcgggcgggcgcccgaaggtcctcc
ggaggcccggcattctgcacgcttcaaaagcgcacgtctgccgcgctgttctcctcttc
ctcatctccgggcctttcgacctgcagcccggtggacagcaagcgaaccggaattgcca
gctggggcgccctctggtaaggttgggaagccctgcaaagtaaactggatggcttttctt
gccgccaaggatctgatggcgcaggggatcaagatctgatcaagagacaggatgaggat

Figure 2B-04

```
cgtttcgcatgattgaacaagatggattgcacgcaggttctccggccgcttgggtggag
aggctattcggctatgactgggcacaacagacaatcggctgctctgatgccgcgtgtt
ccggctgtcagcgcaggggcgcccggttcttttgtcaagaccgacctgtccggtgccc
tgaatgaactgcaggacgaggcagcgcggctatcgtggctggccacgacgggcgttcct
tgcgcagctgtgctcgacgttgtcactgaagcgggaagggactggctgctattgggcga
agtgccggggcaggatctcctgtcatctcaccttgctcctgccgagaaagtatccatca
tggctgatgcaatgcggcggctgcatacgcttgatccggctacctgcccattcgaccac
caagcgaaacatcgcatcgagcgagcacgtactcggatggaagccggtcttgtcgatca
ggatgatctggacgaagagcatcaggggctcgcgccagccgaactgttcgccaggctca
aggcgcgcatgcccgacggcgaggatctcgtcgtgacccatggcgatgcctgcttgccg
aatatcatggtggaaaatggccgcttttctggattcatcgactgtggccggctgggtgt
ggcggaccgctatcaggacatagcgttggctacccgtgatattgctgaagagcttggcg
gcgaatgggctgaccgcttcctcgtgctttacggtatcgccgctcccgattcgcagcgc
atcgccttctatcgccttcttgacgagttcttctgagcgggactctggggttcgaaatg
accgaccaagcgacgcccaacctgccatcacgagatttcgattccaccgccgccttcta
tgaaaggttgggcttcggaatcgttttccgggacgccggctggatgatcctccagcgcg
gggatctcatgctggagttcttcgccgtttcctgccacagtctgagagctccctggcg
aattcggtaccaataaaagagctttattttcatgatctgtgtgttggtttttgtgtgcg
gcgcgccagcttggcgtgaagttcctattctctagaaagtataggaacttccgctctcc
tgagtaggTGCATGTATATCTTGTAAGTTCTCTAGAGAATGACCCATTTGGATTAGTAA
TCATATACCTTTCATTTCTTTCAGGTTGCTTTGAAATTGAATATGAACCACTTCCTTGA
AGGATCAATATTCCTGTTAAGAGAGAAAAATAAAAGCAATTGAAATAGCATATACTGTG
GTCTCTTCGGAAGTCCTTTTACTAAGCATGAAAGGGAAGATCCTGAGTTTTTATGTTTT
TATGACTGTTTTTAATTTCTCATTTTAAAAATGTAACATCTTATTAACTTGGGGGAACT
TTATACAAGTATACAATGCATGTTGATGACATTCATCCTTCCCACCACGTCCTCACTTC
TCCCAGATCTCCATCACCCAACATTGTGTCCTCTTCATTTTTTTTTAATAGCCCACCA
AGTCTAAGTTGAGTTGCCCATAAACTTGTCGTTATTTGGCCATCCACGTAAGCCACATC
CTTAAAAAATGCTGACTCTCATTCTCCCAGAATCCATCTTCTCAGTTATGGGTGAAGGC
TTGTGAGCCTTCCACTTCATGCTGGAATATGGGGTGTTTCCATTGTTGCAGGACTTATG
CAGGCAACCAGAACTGCAGTGGGCTCAGGAGTGTGTAGTTTTATCATGTTGGGAAGATT
CTGTATTGTTCTAGTTTTCCTCAATCTCTGATTCTTACAATATTTCTATTACCTCTTCT
ACTATTGTCCCTGAGCCTTGTGTAAAGAATAGGAGACTTATGTCCCATTTGTGGCTGAG
AACAATATATCTTGTGAATTTTGACCAATTTTCAGTTTCTGCTCTCACCACCCATAATT
CACAGAAACTTCTGCAGTAAGGTGTGAGAGCTGCAGTAATGTAAGAGACAGAGACATGG
ATTTAGAAAGCCACTTGATACTTAGGCCCCTTGTCAGaataatatatttattataataa
aaGTGAAACATAAAATTTAGCGTGTTTTAATATACATGTGTGAATTGTACACCTAGGTA
TGTGTCTGTCCATATCCTCATGTGCATATGTAGAAGCCGGAGTTCAACCTCAAATATTC
CTTCAGGTTCCACCTACTTTGTTTTTCAAGACATGGTTTCTCATTGGCCTGATGCTTGC
TGATTAATCTAGGATGGCTGTCCAGTAAGCACCATGGATCTCTGTGTGTCTCTGTTTTC
CTCACATTGAGATTAGACATGCATGTCACTGTACCTGTTTTGATGTGGCTTTGTTAGT
TTTGGATATCAAACTCATTGTCCGTAAGCTTACATGTTATCTTTGTTACTCTTCTATGG
GTGTGAAGAGACACCATGACTAAGACAATTTATAAAAGGAAGTATTTAATTAGGGCTT
GCTTACATCTTCAGAGGGTAAATCAGAAATTATGACATCAAGCAGTTATGATATTGGAG
AAATAGCTGAGATTTACATCTTTCTGCACAAGGCAGAAAGACAACTGGGAATGGTATC
AACTTTTAAACCTCAAAACCCACCCCAGTGATACATACCTCCTCCAACAAGACCACAC
TCCCTAATCCTTTCTAAACAGTTCTATAAATTGCAGAAACAAGCATTCAAATATATGCA
CCTATGGGGGTCATTCTCATTCAAAACATAACACATGGAAACCATTTAATTTGCTAAGC
```

Figure 2B-05

```
TTTTGGCCAGCCCTAAATATACGTGATGGCTCAGCACTTTAGAAAAAAGCATGAAGAAT
AGGGGTGATTGAGTCAGCAGTCCTGGTATATCTTGAATGAAAGTGTCCACAGGTTTATG
TTGTATAAATGCCTTAATAGTACCAAGAGAGAAAATTCACCAAATTAATCTAAAATATA
TTTCAACAACTGAATCTGTACATACTGCAGAAGAGTAAGCTCGACTCATTGGAAAAGGA
CATAAACAAAGAATATGTTGTCTCTAAACCCAAAAGCCAGTAATAGTTAATATCCTTA
AAATAGCATTAAAATCATTCTTACATGTTACAAGAACTTTAAAAATAAAAGTCACTACA
AAGTTAAATCTCCCCAAATCTCTTTCTTGTCTGGAAAAACTGAAGATGAAAGAATTCCT
GAGGATTTTAGATGCTCATAGCTCCAGCACACGGCAGAAATGCAAAGGTAGATCCACCG
GACTCCTCGGCTTTGGTAACAGTAGCACTTGCACAAAAATAAATTCTGAGTCAGGATCA
GAGACTAGTTAAATCTATTTCTTTTTACTTTATGTCAGGAAGAAAAATCATCTTATGGC
TTTTAGGATAATGGATAGCTGCCACTCTTTCTCTGGCATTACCTCATAGCAAAAATTGA
ACATCATTTCTGATAGGTCCAATAATCACTGAAAGTTCCTTATGTTCGGCCTCCCAACc
acaccacacacacacacacacacacacacacacacacacacagacacacaAAGAGGCCCTC
GAGGCCCACCAACTAATCCCAAGTTTCGTTTCAAAATCTTCTCCCTTCACTTGGCTCCC
ATATATCCTAAGCTCAGAAAATCCAGGCATTGCCATTGTCTGCAACTAGGCTTTGTCAC
ACAACTATGCCTTTGCCATGGTGATTTCTCCTCGTGAAACATACAGTCCTCTAATTCAG
TATTCATATTCAATTTATCTTTTAATAATCATGTTCAATATTATGATCTTCATAAAAA
TATCTCAGTCAAAAAAAATGTCCTCACTATGACCTCCTCCCATAGTACTTTATTTCTG
CGCTTTATAAGTCTAACCATTCTTTGGTCTTTGTTCTTCTTGAGTTTCATGTGTTTTGC
AAATTGTATCTTATATCTTGGGTATTCTAAGTTTCTGGGCTAATATCCACTTATAGCTG
ACACCATTGCATACACTAGCAAGATTTTGCTGAAAGGACCCTGATATAGCTGTCTCTTG
TGAGGCTATGCTGGGGCCTAGCAAACACAGAAGTGGAGGCTCATAGTCAGCTATGATGG
ATCACAGGGCCCCCAATTGAGGAGCTAGAGAAAGTACCCAAGGAGCTAAAGGGATCTGC
AATCCTATAGGTGGAACAACAATATGAACTAACCAGTACCCCTGGAGCTCGTGTCTCT
AGCTGCATATGTATGAGAAGACGGCCATCAGTGGAAAGAGAGGCCCATTGGTCTTGCAA
ACTTTATATGCCTCAGTACAGGGGAACTCCAGGGCCAAGAAGTGGGAGTGGGTGGGTAG
GGGAGTGGGTGGGGGAGGGTATTGTGGACTTTTGGGATAGCATTGGAAATGTAAATGA
AGAAAATACCtaataataataacaatagtaacaataataataataataaAATGAGTCTA
ACCACGCTACAGCTTCTAGTAGAACAGTCCATATCATTTCTGCATCTTACTTAAGCCT
TGGAATATGACATCAATCTAAATGTACTCCAGTCCTTAGATGCTCAGTGACTGCTAAAT
TGAATATATTAACAAGAATTAACAATTCCTAATATTTTAAAAAGAGCATTTTCACACA
TATCAATGTGGAAGGTGGTAAAAGGTTCATTCTCTCAGGAAATGAAATTATTAAAATCA
GTATTTAAATGTTGACAAATTTATTCTATTCAATTACAATTTTAGGGCAGCAAGTTGAG
TAATTTCTTGGCTATCCATTTTCTGCTGTAGGAACTCTAGTCATAATCAAGTCATAAAT
AAAATTTTGTTCTGAATACTACAATTCATACATATTGTTATACATGAATTAGACATTCA
AATTTCTGAGGATTTTAATTTATCTAGTGTTGTGTGGGCTTTTTCTAGAGCAAAATTAT
ATAAAAGACAGTTTGTCCTGTTCACTGTCTCTTCCTACTAACCTGATGGTGAACACAG
CGTAATGCCATGCAGGAAGGAAAGGTACAGAAGTCATCCAACAAATCTCTGTTGGACA
ATGAGCCTTTATTATGTCACAATCGCTGCCCTTGTCTCGGTGGTAAATTATCAGGAAAT
TAGAAAAGTTCTAAGACTGTATCTTTCCACCACAATAAATTTATGCACAGATGAGACCC
TTTGCACCAACCATGGAAACATTGTTCTCTGTGCATCCTGGCTGAAAGTGAAGGTCA
GCGTAATGAGGCACTTAGCTATATTGGTGGACAGAAACTTCTGTCTTCCTTAGTCATTT
GCAgatatcgaattctaccgggtaggggaggcgcttttccaaggcagtctgagcatgcg
cttagcagccccgctggcacttggcgctacacaagtggcctytggcctcgcacacattc
cacatccaccggtaggcgccaaccggctccgttctttggtggccccttcgcgccacctt
ctwctcctcccctagtcaggaagttccccccgcccgcagctcgcgtcgtsaggacgt
gacaaatggaagtagcacgtctcactagtctcgtcagatggacagcaccgctgagcaat
```

Figure 2B-06

```
ggaagcgggtaggcctttggggcagcggccaatagcagctttgctccttcgctttctgg
gctcagaggctgggaaggggtgggtccggggcgggctcagggcgggctcagggcgg
ggcgggcgcccgaaggtcctccggaggcccggcattctgcacgcttcaaaagcgacgt
ctgccgcgctgttctcctcttcctcatctccgggccttcgacctgcaggtcctcgcca
tggatcctgatgatgttgttattcttctaatcttttgtatggaaacttttcttcgtac
cacgggactaaacctggttatgtagattccattcaaaaaggtatacaaaagccaaaatc
tggtacacaaggaaattatgacgatgattggaaagggttttatagtaccgacaataaat
acgacgctgcgggatactctgtagataatgaaaacccgctctctggaaaagctggaggc
gtggtcaaagtgacgtatccaggactgacgaaggttctcgcactaaagtggataatgc
cgaaactattaagaaagagttaggtttaagtctcactgaaccgttgatggagcaagtcg
gaacggaagagtttatcaaaaggttcggtgatggtgcttcgcgtgtagtgctcagcctt
cccttcgctgaggggagttctagcgttaatatattaataactgggaacaggcgaaagc
gttaagcgtagaacttgagattaattttgaaacccgtggaaaacgtggccaagatgcga
tgtatgagtatatggctcaagcctgtgcaggaaatcgtgtcaggcgatctctttgtgaa
ggaaccttacttctgtggtgtgacataattggacaaactacctacagagatttaaagct
ctaaggtaaatataaaattttaagtgtataatgtgttaaactactgattctaattgtt
tgtgtattttagattccaacctatggaactgatgaatgggagcagtggtggaatgcaga
tcctagagctcgctgatcagcctcgactgtgccttctagttgccagccatctgttgttt
gcccctcccccgtgccttccttgaccctggaaggtgccactcccactgtccttcctaa
taaaatgaggaaattgcatcgcattgtctgagtaggtgtcattctattctgggggtgg
ggtggggcaggacagcaaggggaggattgggaagacaatagcaggcatgctgggatg
cggtgggctctatggcttctgaggcggaagaaccagctggggctcgacctcgagggg
ggcccggtacccagcttttgttccctagtgagggttaattgcgcgcttggcgtaatc
atggtcatagctgtttcctgtgtgaaattgttatccgctcacaattccacacaacatac
gagccggaagcataaagtgtaaagcctggggtgcctaatgagtgagctaactcacatta
attgcgttgcgctcactgcccgctttccagtcgggaaacctgtcgtgccagctgcatta
atgaatcggccaacgcgcggggagaggcggtttgcgtattgggcgctcttccgcttcct
cgctcactgactcgctgcgctcggtcgttcggctgcggcgagcggtatcagctcactca
aaggcggtaatacggttatccacagaatcaggggataacgcaggaaagaacatgtgagc
aaaaggccagcaaaaggccaggaaccgtaaaaaggccgcgttgctggcgttttccata
ggctccgcccccctgacgagcatcacaaaaatcgacgctcaagtcagaggtggcgaaac
ccgacaggactataaagataccaggcgtttccccctggaagctccctcgtgcgctctcc
tgttccgaccctgccgcttaccggatacctgtccgcctttctcccttcgggaagcgtgg
cgctttctcatagctcacgctgtaggtatctcagttcggtgtaggtcgttcgctccaag
ctgggctgtgtgcacgaaccccccgttcagcccgaccgctgcgccttatccggtaacta
tcgtcttgagtccaacccggtaagacacgacttatcgccactggcagcagccactggta
acaggattagcagagcgaggtatgtaggcggtgctacagagttcttgaagtggtggcct
aactacggctacactagaaggacagtatttggtatctgcgctctgctgaagccagttac
cttcggaaaagagttggtagctcttgatccggcaaacaaaccaccgctggtagcggtg
gttttttgtttgcaagcagcagattacgcgcagaaaaaaggatctcaagaagatcct
ttgatcttttctacggggtctgacgctcagtggaacgaaaactcacgttaagggatttt
ggtcatgagattatcaaaaggatcttcacctagatcctttaaattaaaaatgaagtt
ttaaatcaatctaaagtatatgagtaaacttggtctgacagttaccaatgcttaatc
agtgaggcacctatctcagcgatctgtctatttcgttcatccatagttgcctgactccc
cgtcgtgtagataactacgatacgggagggcttaccatctggccccagtgctgcaatga
taccgcgagacccacgctcaccggctccagatttatcagcaataaaccagccagccgga
agggccgagcgcagaagtggtcctgcaactttatccgcctccatccagtctattaattg
```

Figure 2B-07

```
ttgccgggaagctagagtaagtagttcgccagttaatagtttgcgcaacgttgttgcca
ttgctacaggcatcgtggtgtcacgctcgtcgtttggtatggcttcattcagctccggt
tcccaacgatcaaggcgagttacatgatccccatgttgtgcaaaaaagcggttagctc
cttcggtcctccgatcgttgtcagaagtaagttggccgcagtgttatcactcatggtta
tggcagcactgcataattctcttactgtcatgccatccgtaagatgcttttctgtgact
ggtgagtactcaaccaagtcattctgagaatagtgtatgcggcgaccgagttgctcttg
cccggcgtcaatacgggataataccgcgccacatagcagaactttaaaagtgctcatca
ttggaaaacgttcttcggggcgaaaactctcaaggatcttaccgctgttgagatccagt
tcgatgtaacccactcgtgcacccaactgatcttcagcatcttttactttcaccagcgt
ttctgggtgagcaaaaacaggaaggcaaaatgccgcaaaaaagggaataagggcgacac
ggaaatgttgaatactcatactcttccttttcaatattattgaagcatttatcaggg
tattgtctcatgagcggatacatatttgaatgtatttagaaaaataaacaaatagggt
tccgcgcacatttccccgaaaagtgccacctaaattgtaagcgttaatattttgttaaa
attcgcgttaaattttgttaaatcagctcatttttaaccaataggccgaaatcggca
aaatcccttataaatcaaaagaatagaccgagatagggttgagtgttgttccagtttgg
aacaagagtccactattaaagaacgtggactccaacgtcaaagggcgaaaaaccgtcta
tcagggcgatggcccactacgtgaaccatcaccctaatcaagttttttggggtcgaggt
gccgtaaagcactaaatcggaaccctaaagggagccccgatttagagcttgacgggga
aagccggcgaacgtggcgagaaaggaagggaagaaagcgaaaggagcgggcgctagggc
gctggcaagtgtagcggtcacgctgcgcgtaaccaccacacccgccgcgcttaatgcgc
cgctacagggcgcgtcccattcgccattcaggctgcgcaactgttgggaagggcgatcg
gtgcgggcctcttcgctattacgccagctggcgaaaggggatgtgctgcaaggcgatt
aagttgggtaacgccagggttttcccagtcacgacgttgtaaaacgacggccagtgagc
gcgcgtaatacgactcactatagggcgGCCGCTACTTGGAGAACTACTGGCAATTATTA
ATGTCTGAGGGAAGTGATACTTTTTTCTCCAGTTGGGTAGCTGGTGATTAATTTCTCAT
GACTGGTGAATTACTTGCAAACAACTCTAAACTCAGTGAGTCATCCAAAAAGAAGGCTA
TTTTATGTCAATCAGATATTCCAGC
```

METHODS FOR TREATING DISORDERS THAT INVOLVE IMMUNOGLOBULIN A

CROSS-REFERENCE TO RELATED APPLICATIONS

This application is the §371 U.S. National Stage of International Application No. PCT/IB2012/000053, filed Jan. 17, 2012, which claims the benefit of U.S. Provisional Application Ser. No. 61/433,449, filed Jan. 17, 2011, which are incorporated by reference herein in their entireties.

BACKGROUND

IgA nephropathy (IgAN), also known as Berger disease, is the most common cause of chronic glomerulonephritis and leads to end stage kidney failure in about 25% of cases. Twenty to forty percent of IgAN patients receiving kidney transplants suffer disease recurrence within 5 years of transplant. The onset of IgAN has been associated with upper respiratory tract infections that trigger the mucosal immune system. As a result of hyper-reactivity of the mucosal immune system, B cells produce increased amounts of IgA leading to IgA deposition in kidney glomeruli. IgA deposition leads to glomerular inflammation, resulting in kidney dysfunction, hypertension and slow progression towards kidney failure.

Current treatments for IgAN are aimed at slowing kidney damage and include anti-hypertensives to control blood pressure and steroid treatment to reduce inflammation. Long term dialysis and kidney transplantation are used to treat end stage kidney failure but have a large negative impact on patient quality of life. Currently, no specific treatment is available to correct hyper-active mucosal immune responses or reduce IgA levels.

Research into pathological mechanisms and new treatments for IgAN have been hampered by lack of appropriate animal models. Currently reported mouse models for IgAN include a multigenic outbred model with variable disease progression (ddY mouse), a single gene knockout that affects IgA deposition but not IgA production (uteroglobulin knockout), and a recently reported mouse transgenic for a B cell activating factor (BAFF transgenic). None of these models selectively impact on IgA production and have to date not been widely adopted for IgAN studies.

IgAN is estimated to affect over 60,000 people in the US, and several fold higher incidence of IgAN is reported among Asian populations. IgAN is incurable and the current limited treatment options include management of hypertension and administering non-specific anti-inflammatories in order to delay the need for dialysis or transplantation. No targeted therapies for reducing IgA production are available.

SUMMARY OF THE INVENTION

The invention relates to the discovery and characterization of polypeptides that play a role in the production of IgA, and to the generation of an animal model that exhibits IgA nephropathy. The compositions and methods embodied in the present invention are particularly useful for drug screening and/or treatment of disorders that involve IgA.

Provided herein are uses of an FDC-SP polypeptide and a pharmaceutically acceptable carrier. In one embodiment, the use is in the manufacture of a medicament for treating an IgA mediated condition. In one embodiment, the use is for treating an IgA mediated condition. An example of such a condition includes a glomerulonephritis, such as IgA nephropathy and Henoch-Schönlein purpura. Another example of such a condition includes IgA pemphigus. In one embodiment, the use is in the manufacture of a medicament for decreasing IgA concentration. In one embodiment, the use is for decreasing IgA concentration.

The FDC-SP polypeptide may include an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 90% amino acid similarity with SEQ ID NO:2 or SEQ 11) NO:4. The FDC-SP polypeptide may include an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 90% amino acid similarity with a subset of consecutive amino acids chosen from SEQ ID NO:2 or 4.

Also provided herein are methods of using an FDC-SP polypeptide. In one embodiment, a method includes altering IgA concentration in a subject by administering to the subject in need thereof an effective amount of an FDC-SP polypeptide, wherein the FDC-SP polypeptide results in a decreased IgA level in the subject compared to the subject before the administration. The IgA level may be decreased, for instance, in serum, in bronchoalveolar lavage fluid, in saliva, or a combination thereof. The method may further include identifying a subject having or at risk of an IgA mediated condition. The decrease may be a decrease of at least 10%.

The FDC-SP polypeptide may include an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 90% amino acid similarity with SEQ ID NO:2 or SEQ ID NO:4. The FDC-SP polypeptide may include an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 90% amino acid similarity with a subset of consecutive amino acids chosen from SEQ ID NO:2 or 4.

In one embodiment, a method includes treating a subject by administering to the subject an effective amount of a FDC-SP polypeptide, wherein the subject has signs of a disorder that includes excessive IgA production. An example of such a disorder includes a glomerulonephritis, such as IgA nephropathy and Henoch-Schönlein purpura. Another example of such a disorder includes IgA pemphigus.

Provided herein is an animal that has decreased expression of an endogenous FDC-SP coding sequence, and which develops pathophysiological features of IgA nephropathy selected from IgA deposition in kidneys, mesangial hyperproliferation, and polypeptide deposition in glomeruli. Also provided herein is an animal that has decreased expression of an endogenous FDC-SP coding sequence, wherein the animal has at least one of the following: increased IgA in serum, saliva, bronchoalveolar lavage fluid, or a combination thereof; increased IgA expressing B lymphocytes in circulation, lymphoid tissue, or a combination thereof; or increased IgA production in vitro by isolated B lymphocytes; wherein the increase is compared to a control mouse. In one embodiment, the animal may have a heterozygous disruption of an endogenous FDC-SP coding sequence. In one embodiment, the animal may have a homozygous disruption of an endogenous FDC-SP coding sequence. In one embodiment, the animal is not a human. In one embodiment, the animal is a mouse.

Also provided herein is a cell from the animal, wherein the cell has decreased expression of an endogenous FDC-SP coding sequence. Examples of such cells include, but are not limited to, a follicular dendritic cell, a monocyte, or a macrophage. Also provided herein is a tissue from the animal. The tissue may be, but is not limited to, lymphoid tissue.

Provided herein are methods for identifying a compound that decreases the concentration of IgA in an animal. In one embodiment, the method includes administering to an animal a compound, and measuring the concentration of IgA, wherein a decreased concentration of IgA in an animal administered the compound compared to the concentration of IgA before the administration indicates the compound decreases the concentration of IgA in an animal. The concentration of IgA may be decreased, for instance, in serum, saliva, bronchoalveolar lavage fluid, or a combination thereof. The concentration of IgA may be measured by determining the number of IgA expressing B lymphocytes in circulation, lymphoid tissue, or a combination thereof, of the animal. A decrease in the number of IgA expressing B lymphocytes indicates a decreased concentration of IgA in the animal.

Provided herein are methods for identifying a compound that treats a condition associated with increased levels of IgA. In one embodiment, the method includes administering to an animal a compound, wherein the animal displays a sign of a condition associated with increased levels of IgA, and evaluating a sign of a condition associated with increased levels of IgA, wherein a decrease in the presence of a sign indicates treats a condition associated with increased levels of IgA. The sign may be selected from IgA deposition in kidneys, mesangial hyperproliferation, polypeptide deposition in glomeruli, proteinurea, or a combination thereof. The animal may include decreased expression of an FDC-SP polypeptide.

Also provided herein are polypeptides. In one embodiment, a polypeptide has immuno-modulatory activity, and includes an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the isolated polypeptide either (1) comprises no greater than 40 amino acids, or (2) comprises greater than 45 amino acids. In one embodiment, a polypeptide has immuno-modulatory activity, and includes an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 90% amino acid and no greater than 99% similarity with SEQ ID NO:2 or SEQ ID NO:4. In one embodiment, a polypeptide has immuno-modulatory activity, and includes an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 90% similarity with a subset of consecutive amino acids chosen from SEQ ID NO:2 or 4.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, enzyme, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring. An "isolated" polypeptide is one that has been removed from a cell. For instance, an isolated polypeptide is a polypeptide that has been removed from the cytoplasm a cell, and many of the polypeptides, nucleic acids, and other cellular material of its natural environment are no longer present. A "purified" polypeptide is one that is at least 60% free, preferably at least 75% free, and most preferably at least 90% free from other components of a cell.

As used herein, a polypeptide may be "structurally similar" to a reference polypeptide if the amino acid sequence of the polypeptide possesses a specified amount of sequence similarity and/or sequence identity compared to the reference polypeptide. Thus, a polypeptide may be "structurally similar" to a reference polypeptide if, compared to the reference polypeptide, it possesses a sufficient level of amino acid sequence identity, amino acid sequence similarity, or a combination thereof.

As used herein, the term "polynucleotide" refers to a polymeric form of nucleotides of any length, either ribonucleotides, deoxynucleotides, peptide nucleic acids, or a combination thereof, and includes both single-stranded molecules and double-stranded duplexes. A polynucleotide can be obtained directly from a natural source, or can be prepared with the aid of recombinant, enzymatic, or chemical techniques. A polynucleotide described herein may be isolated. An "isolated" polynucleotide is one that has been removed from its natural environment. Polynucleotides that are produced by recombinant, enzymatic, or chemical techniques are considered to be isolated and purified by definition, since they were never present in a natural environment.

A "regulatory sequence" is a nucleotide sequence that regulates expression of a coding sequence to which it is operably linked. Nonlimiting examples of regulatory sequences include promoters, enhancers, transcription initiation sites, translation start sites, translation stop sites, transcription terminators, and poly(A) signals. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

The term "complementary" refers to the ability of two single stranded polynucleotides to base pair with each other, where an adenine on one polynucleotide will base pair to a thymine or uracil on a second polynucleotide and a cytosine on one polynucleotide will base pair to a guanine on a second polynucleotide.

Conditions that are "suitable" for an event to occur, or "suitable" conditions are conditions that do not prevent such events from occurring. Thus, these conditions permit, enhance, facilitate, and/or are conducive to the event.

As used herein, an antibody that can "specifically bind" a polypeptide is an antibody that interacts only with the epitope of the antigen that induced the synthesis of the antibody, or interacts with a structurally related epitope. An antibody that "specifically binds" to an epitope will, under the appropriate conditions, interact with the epitope even in the presence of a diversity of potential binding targets.

As used herein, "ex vivo" refers to a cell that has been removed from the body of an animal. Ex vivo cells include, for instance, primary cells (e.g., cells that have recently been removed from a subject and are capable of limited growth in tissue culture medium), and cultured cells (e.g., cells that are capable of long term culture in tissue culture medium).

As used herein, "B cell" refers to lymphocytes that are able to produce antibody that specifically bind an epitope of an antigen. Examples of B cells include plasma B cells, memory B cells, B-1 cells, B-2 cells, marginal zone B cells, and follicular B cells. A B cell may include surface antigens such as CD19, CD20, CD21, CD22, CD23, surface immunoglobulin, Ig-alpha (also known as CD79A), and Ig-beta (also known as CD79B).

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. A, Amino acid sequence of a mouse FDC-SP polypeptide, mFDC-SP (SEQ ID NO:6), a rat FDC-SP polypeptide, rFDC-SP (SEQ ID NO:7), a human FDC-SP polypeptide, hFDC-SP (SEQ ID NO:8), and a chimpanzee FDC-SP polypeptide, cFDC-SP (SEQ ID NO:9). The site of cleavage of the secretion signal is shown by the arrow. B, Nucleotide sequence of human FDC-SP mRNA (SEQ ID NO:10).

Bronchoalveolar lavage (BALF) fluid was collected by flushing lungs with 10 mL of PBS. Levels of the indicated antibody isotypes were measured using specific ELISA assays.

Figure 5:
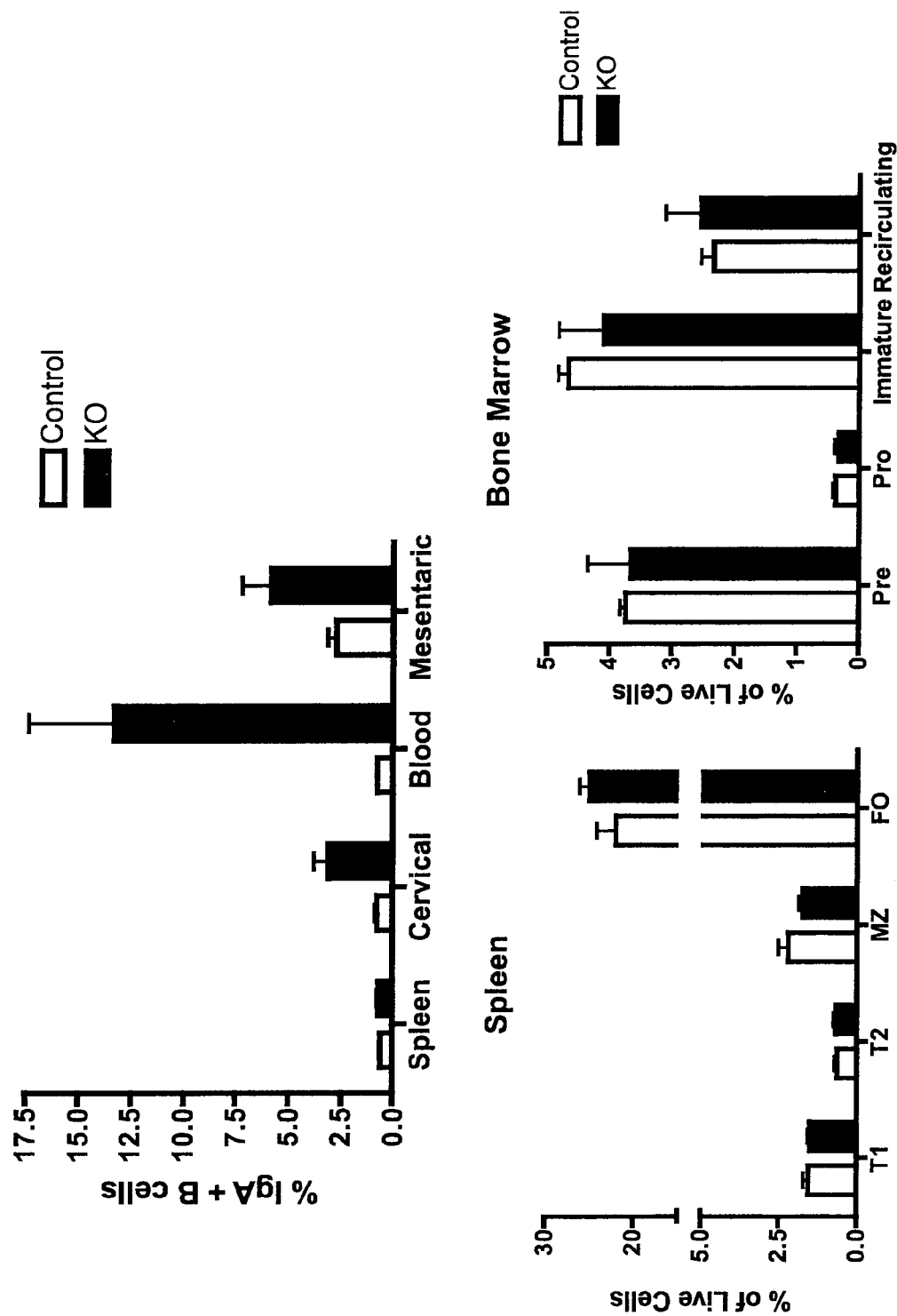

FIG. 5. Mesentaric lymph node, cervical lymph node, spleen, and blood cells were collected from young adult FDC-SP KO mice and frequency of IgA+B lymphocytes were measured by flow cytometry. Bottom panels represent results from additional flow cytometry analyses which indicate otherwise normal B cell subset composition in FDC-SP KO mice. Graphs represent mean and SEM of 4 mice per genotype. Cervical and mesentaric refer to lymph nodes. T1, transitional type 1, gated as B220+IgM+CD23-CD21- lymphocytes; T2, transitional type 2, gated as B220+IgM+CD23+CD21+ lymphocytes; MZ, marginal zone, gated as B220+IgM+CD23-CD21+ lymphocytes; FO, follicular or B2 cells, gated as B220+IgM+CD23+CD21- lymphocytes; pre, pre-B cells, gated as B220+IgM-CD43-lymphocytes; pro, pro-B, gated as B220+IgM-CD43+ lymphocytes; Immature, immature B cells, gated as B220+IgM++CD43- lymphocytes; Mature, mature recirculating B cells, gated as B220++IgM++CD43- lymphocytes.

Figure 6:
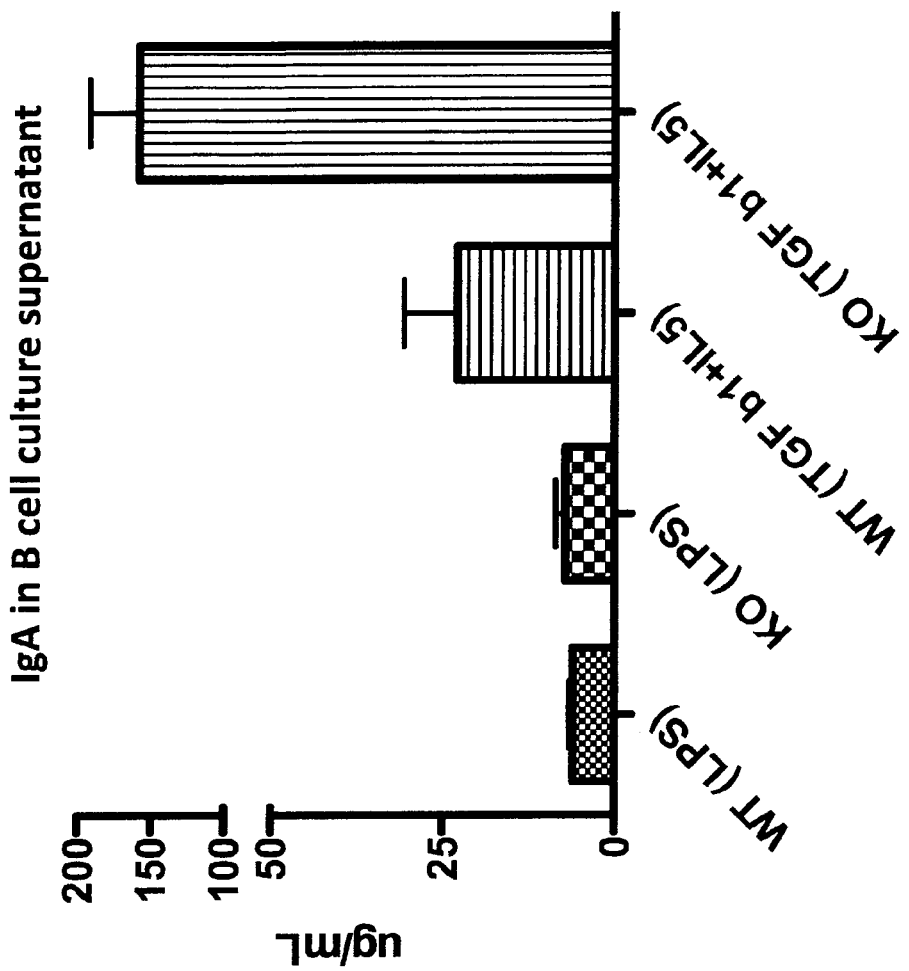

FIG. 6. B cells were purified from spleens of control (WT) or FDC-SP KO mice using negative selection with anti-CD43 coupled magnetic beads. Cells were cultured for 5 days with the indicated stimuli, supernatants were harvested and IgA production was assessed by ELISA assays.

Figure 7:
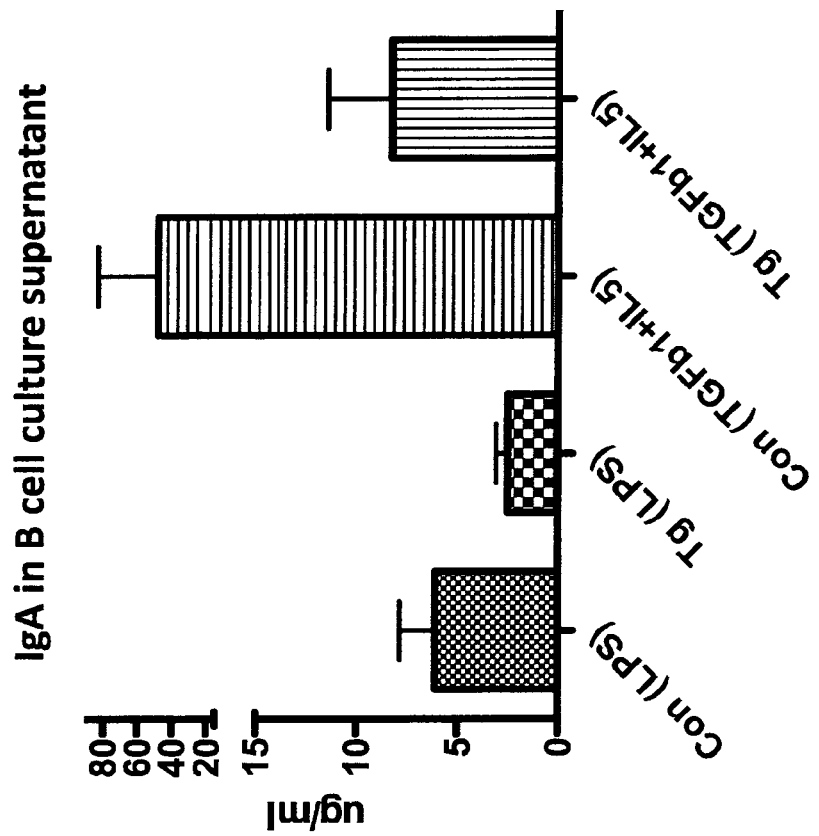

FIG. 7. B cells were purified from spleens of control or FDC-SP TG mice using negative selection with anti-CD43 coupled magnetic beads. Cells were cultured for 5 days with the indicated stimuli, supernatants were harvested and IgA production was assessed by ELISA assays.

Figure 8:
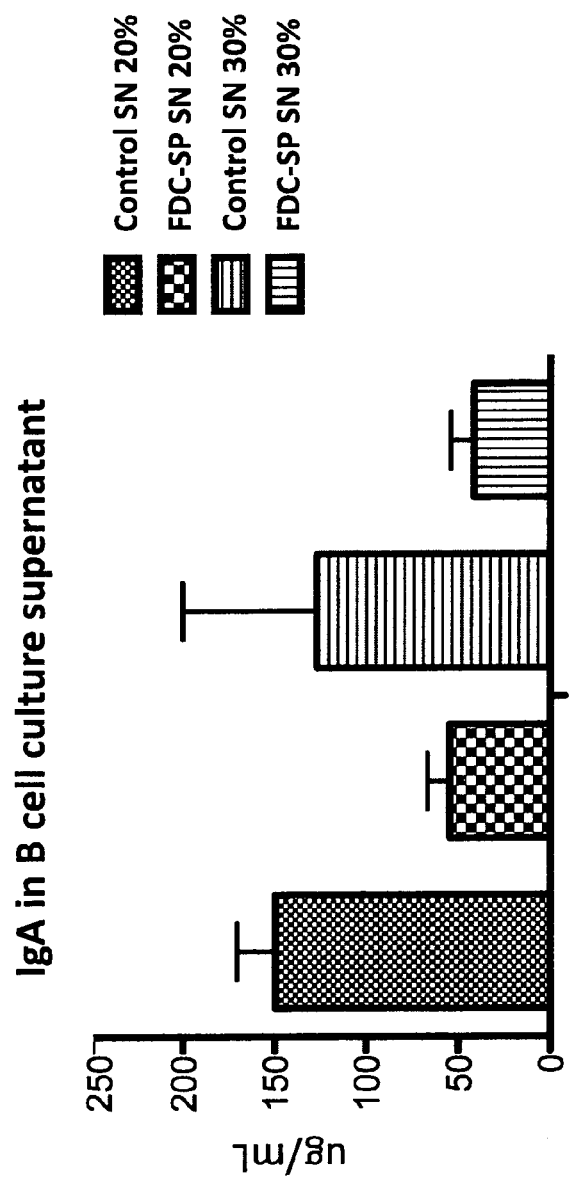

FIG. 8. B cells were purified from spleens of C57BL6 mice using negative selection with anti-CD43 coupled magnetic beads. Cells were cultured for 5 days with the indicated stimuli and the indicated percentage of a supernatant containing recombinant FDC-SP (FDC-SP SN) or a control supernatant (Control SN). The resulting levels of IgA production by the cultured cells were measured by ELISA assay.

Figure 9:
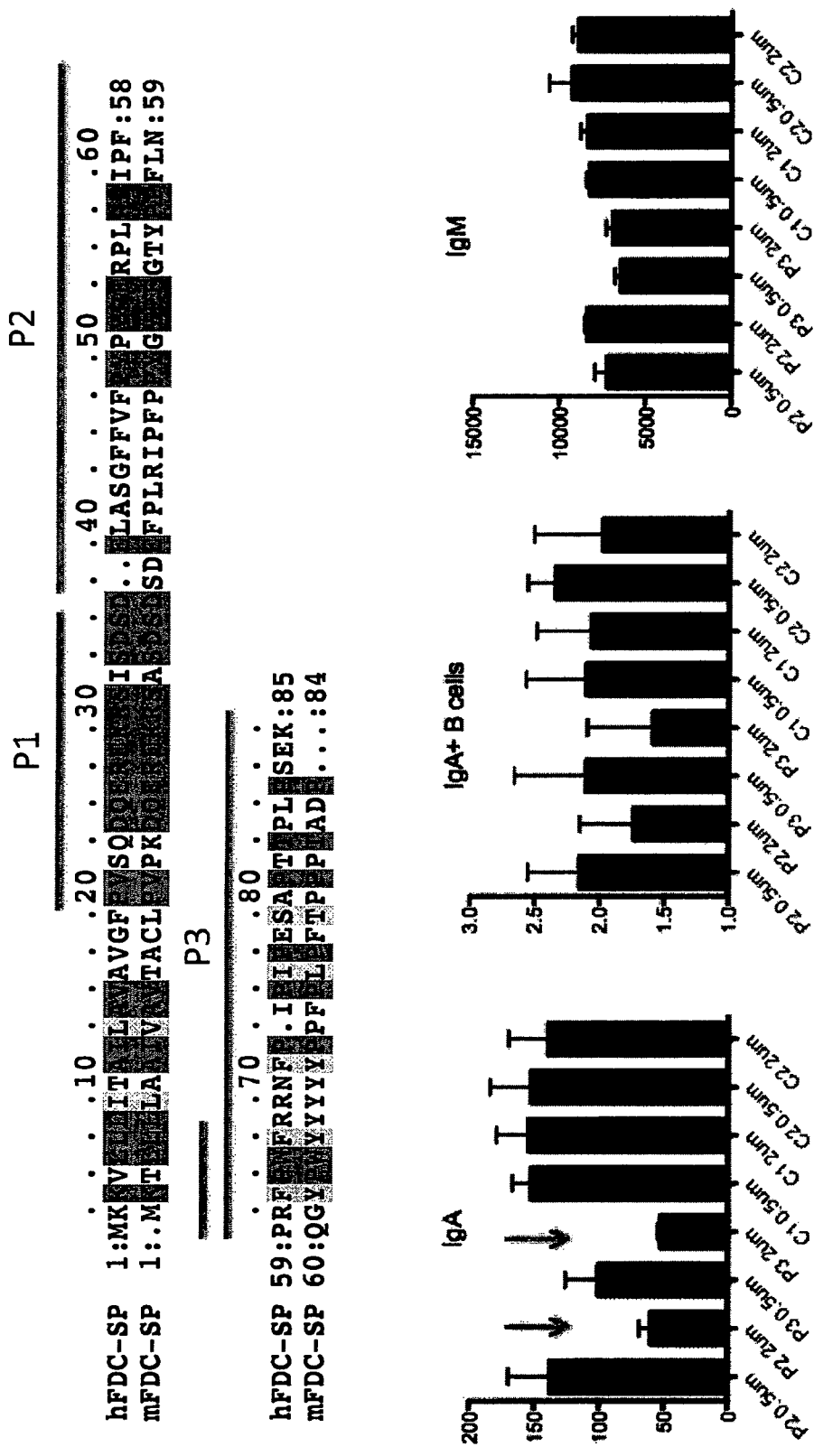

FIG. 9. The indicated synthetic peptides P1-P3 corresponding to mouse FDC-SP were added at the indicated concentrations to cultures of mouse B cells stimulated to produce IgA (TGFb1+IL-5). The resulting levels of IgA or IgM production were assessed by ELISA assays of culture supernatants. Percentage of cultured cells expressing IgA was also determined by flow cytometry (middle graph). P1 corresponds to amino acids 18-33 of mFDC-SP, P2 corresponds to amino acids 35-65 of mFDC-SP, and P3 corresponds to amino acids 60-84 of FDC-SP. Note that peptide P1 had no effect. Control peptides C1 and C2 were scrambled versions of corresponding FDC-SP derived peptides. hFDC-SP, human FDC-SP; mFDC-SP, mouse FDC-SP; urn, micromolar.

Figure 10A:
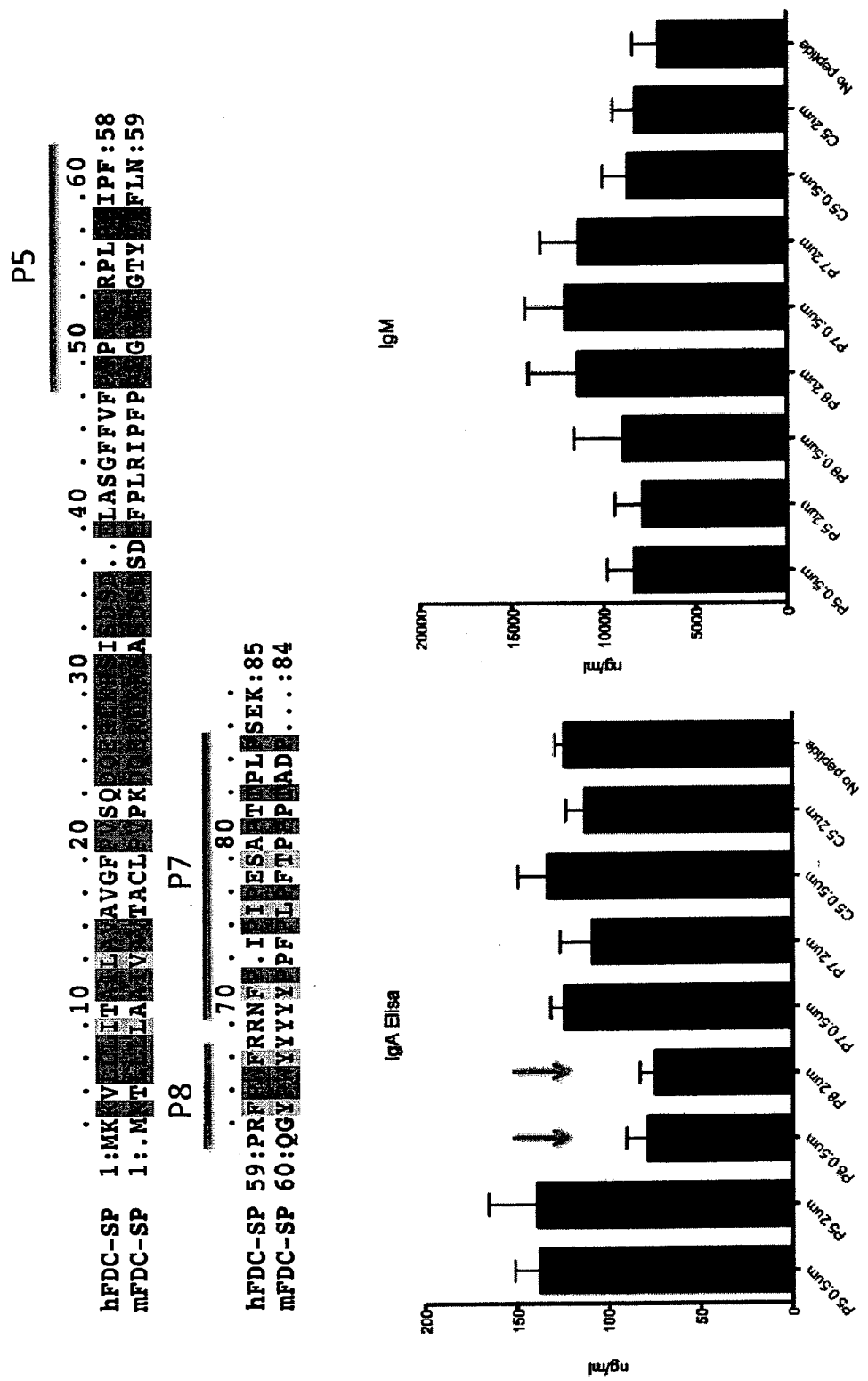
Figure 10B:
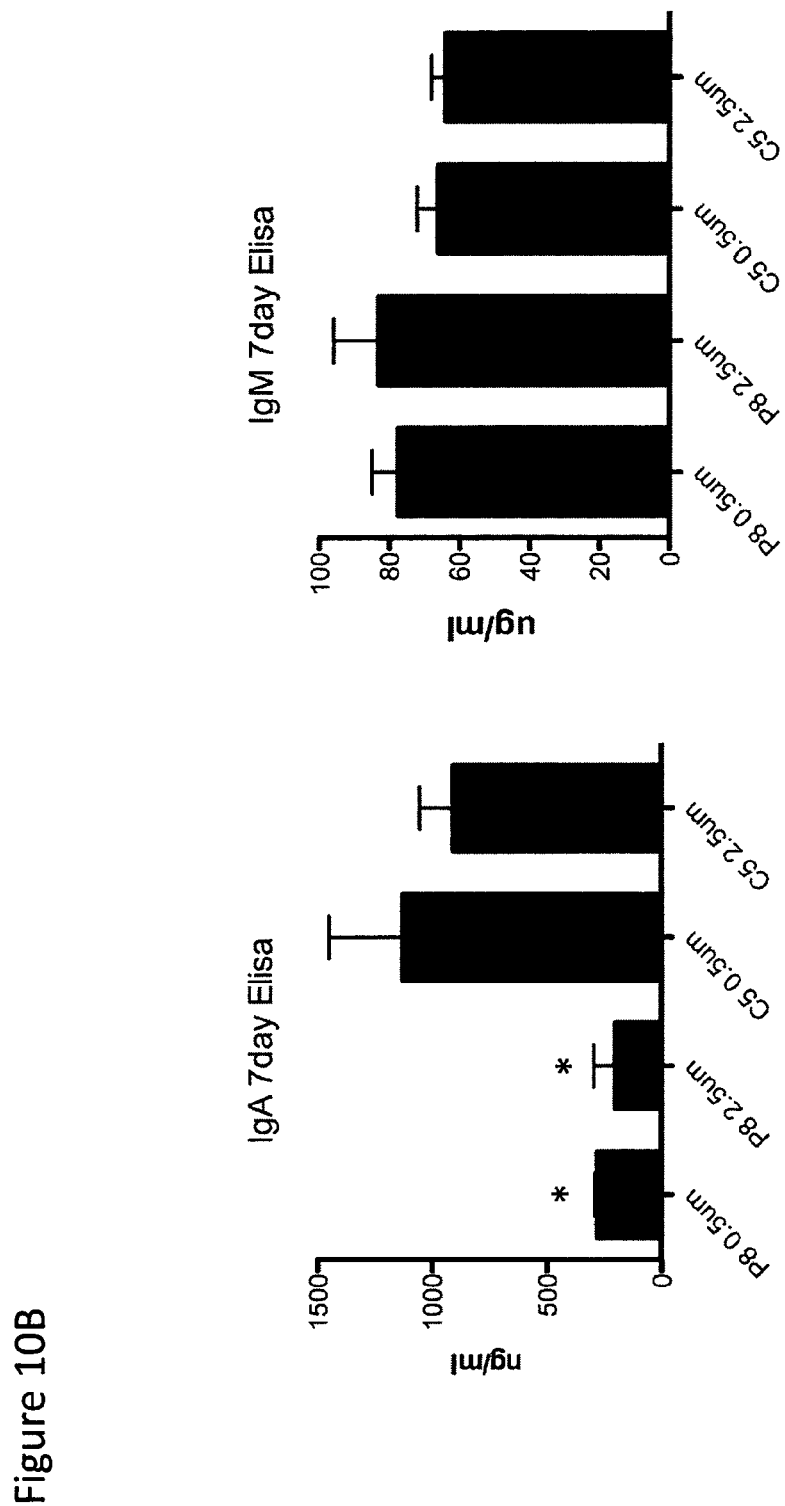

FIG. 10. The effect of the indicated synthetic peptides on IgA or IgM production were assessed by ELISA assays of culture supernatants collected after 5 days of culture (A) or 7 days of culture (B). Control peptide C5 was a scrambled version of P8. hFDC-SP, human FDC-SP; mFDC-SP, mouse FDC-SP; um, micromolar. P5 corresponds to amino acids 46-59 of mFDC-SP, P7 corresponds to amino acids 68-84 of mFDC-SP, and P8 corresponds to amino acids 60-65 of FDC-SP.

Figure 11:
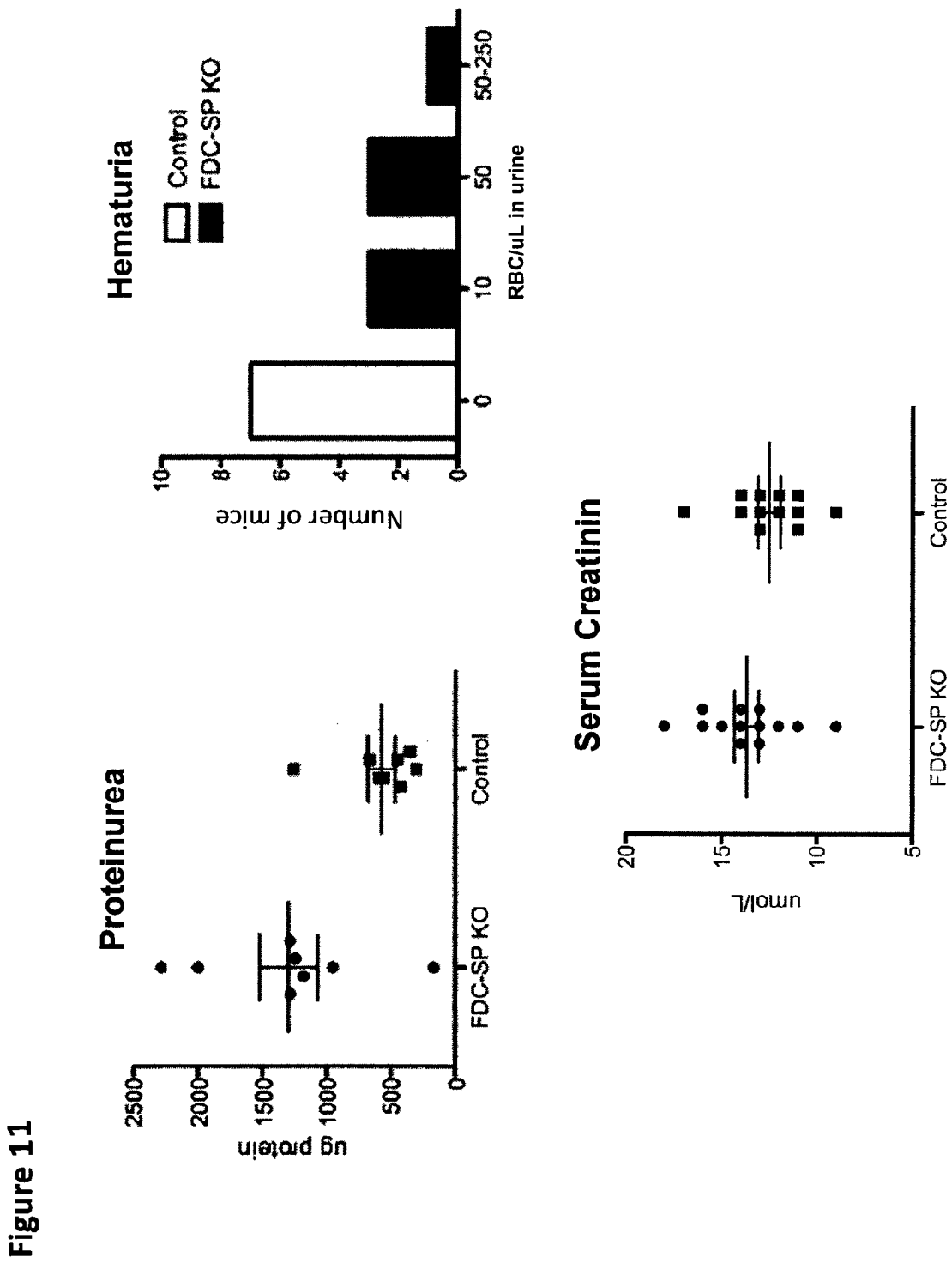

FIG. 11. Urine or serum collected from mice greater than one year old were assessed for the indicated biomarkers of kidney dysfunction.

Figure 12:
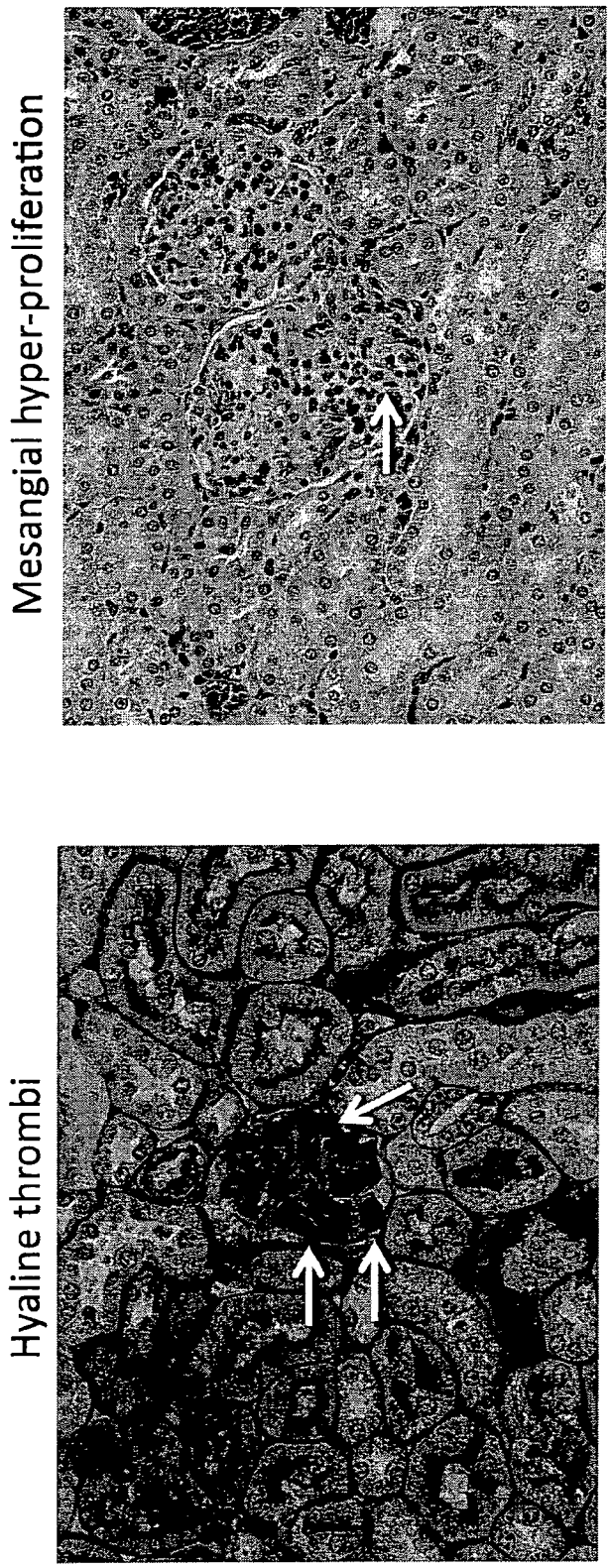

FIG. 12. Kidneys from FDC-SP KO mice were assessed for abnormal histology by staining sections of formalin-fixed kidney with H&E or PAS stain.

Figure 13:
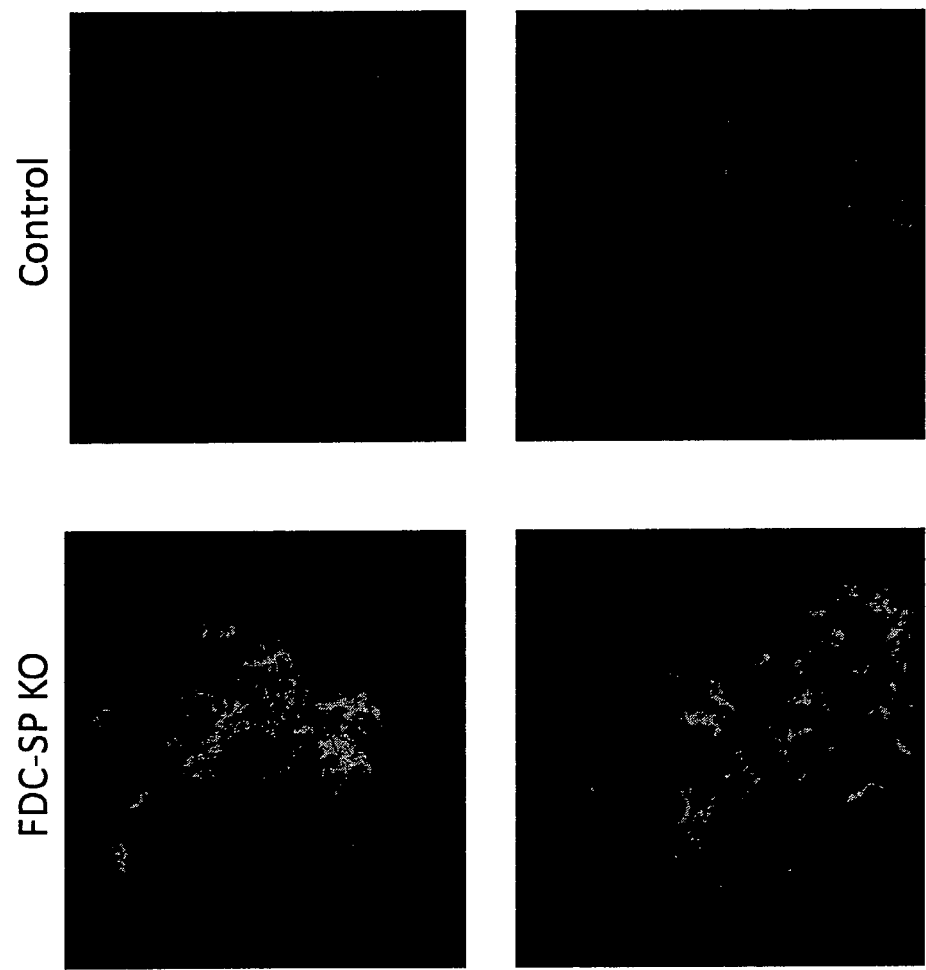

FIG. 13. Kidney cryosections stained with FITC-labeled anti-IgA.

DETAILED DESCRIPTION OF ILLUSTRATIVE EMBODIMENTS

The present invention includes, but is not limited to, isolated polypeptides having immuno-modulatory activity. A polypeptide having immuno-modulatory activity is referred to herein as an FDC-SP polypeptide. An FDC-SP polypeptide is expressed by activated follicular dendritic cells (FDCs) from tonsils and TNF-α-activated FDC-like cell lines, such as FDC-1 and but not by B cell lines, primary germinal center B cells, or anti-CD40 plus IL-4-activated B cells. FDC-SP is also expressed in leukocyte-infiltrated tonsil crypts and by LPS- or *Staphylococcus aureus* Cowan strain 1-activated leukocytes. FDC-SP is posttranslationally modified and secreted and can bind to the surface of B lymphoma cells, but not T lymphoma cells, and binding of FDC-SP to primary human B cells is markedly enhanced upon activation with the T-dependent activation signals such as anti-CD40 plus IL-4 (Marshall et al., 2002, J. Immunol., 169:2381-2389).

In one embodiment, an FDC-SP polypeptide is $X_1X_2X_3ProTrpX_4$ (SEQ ID NO:1), wherein $X_1$ and $X_2$ are any amino acid, $X_3$ is Tyr, Phe, or Asn, and $X_4$ is Tyr or Phe. As described in Example 1, this 6-mer has been found to have immuno-modulatory activity. In one embodiment, an FDC-SP polypeptide includes SEQ ID NO:1. In one embodiment, an FDC-SP polypeptide with SEQ ID NO:1 has a number of amino acids that is no greater than any number selected from an integer between 6 and 70, i.e., no greater than a number selected from 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 amino acids in length. In one embodiment, an FDC-SP polypeptide with SEQ ID NO:1 has a number of amino acids that includes or is greater than any number selected from an integer between 6 and 70, i.e., includes or is greater than a number selected from 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 amino acids in length. In one embodiment, an FDC-SP polypeptide with SEQ ID NO:1 has a number of amino acids selected from an integer between 6 and 70, i.e., is 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 amino acids in length.

Examples of FDC-SP polypeptides that include SEQ ID NO:1 are depicted at SEQ ID NO:2 (see amino acids 21-84 of SEQ ID NO:6 in FIG. 1, which is encoded by nucleotides 121-314 of the mRNA disclosed in the Genbank database at accession number BC037156), SEQ ID NO:3 (see amino acids 21-81 of SEQ ID NO:7 in FIG. 1, which is also available from the Genbank database at accession number BAD77806.1), SEQ ID NO:4 (see amino acids 22-85 of SEQ ID NO:8, which is also available from the Genbank database at accession number AAN01116, and is encoded by nucleotides 49-306 of the mRNA disclosed in the Genbank database at accession number AF435080 [SEQ ID NO:10]), and SEQ ID NO:5 (see amino acids 22-85 of SEQ ID NO:9, which is also available from the Genbank database at accession number XP_001160925.1). Other examples of FDC-SP polypeptides that include SEQ ID NO:1 are amino acids 34-65 and 60-84 of SEQ ID NO:6 and 35-64 and 59-85 of SEQ ID NO:8.

Other examples of FDC-SP polypeptides of the present invention include those that are structurally similar to the amino acid sequence of SEQ ID NO:2, 3, 4, and/or 5, or a subset of consecutive amino acids chosen from SEQ ID NO:2, 3, 4, or 5 provided the subset includes SEQ ID NO:1. An FDC-SP polypeptide having structural similarity with the amino acid sequence of SEQ ID NO: 2, 3, 4, and/or 5, or having structural similarity with a subset of consecutive amino acids chosen from SEQ ID NO:2, 3, 4, or 5, has immuno-modulatory activity.

Structural similarity of two polypeptides can be determined by aligning the residues of the two polypeptides (for example, a candidate polypeptide and any appropriate reference polypeptide described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference polypeptide may be a polypeptide described herein. In one embodiment, a reference polypeptide is a full-length FDC-SP polypeptide, such as SEQ ID NO:6, 7, 8, or 9. In one embodiment, a reference polypeptide is an FDC-SP polypeptide that has been post-translationally processed to delete the signal sequence, for instance, SEQ ID NO:2, 3, 4, or 5. In one embodiment, a reference polypeptide includes a subset of consecutive amino acids chosen from SEQ ID NO:2, 3, 4, or 5 provided the subset includes SEQ ID NO:1 (e.g., provided the subset includes amino acids 40-45 of SEQ ID NO:2 if SEQ ID NO:2 is the reference sequence, amino acids 36-41 of SEQ ID NO:3 if SEQ ID NO:3 is the reference sequence, amino acids 38-43 of SEQ ID NO:4 if SEQ ID NO:4 is the reference sequence, or amino acids 38-43 of SEQ ID NO:5 if SEQ ID NO:5 is the reference sequence. A candidate polypeptide is the polypeptide being compared to the reference polypeptide. Thus, in one embodiment, a candidate polypeptide may be between 6 and 70 amino acids in length. A candidate polypeptide may be isolated, for example, from a cell, such as a human or mouse cell, or can be produced using recombinant techniques, or chemically or enzymatically synthesized. A candidate polypeptide may be inferred from a nucleotide sequence present in the genome of a cell.

Unless modified as otherwise described herein, a pair-wise comparison analysis of amino acid sequences can be carried out using the Blastp program of the blastp suite-2sequences search algorithm, as described by Tatiana et al., (*FEMS Microbiol Lett*, 174, 247-250 (1999)), and available on the National Center for Biotechnology Information (NCBI) website. The default values for all blastp suite-2sequences search parameters may be used, including general paramters: expect threshold=10, word size=3, short queries=on; scoring parameters: matrix=BLOSUM62, gap costs=existence:11 extension:1, compositional adjustments=conditional compositional score matrix adjustment. Alternatively, polypeptides may be compared using the BESTFIT algorithm in the GCG package (version 10.2, Madison Wis.).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a polypeptide described herein may be selected from other members of the class to which the amino acid belongs.

Thus, as used herein, a candidate polypeptide useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence.

Alternatively, as used herein, a candidate polypeptide useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

In one embodiment, an FDC-SP polypeptide includes a highly charged N-terminal region adjacent to and downstream of the secretion signal, and a moderately proline-rich central region. The highest degree of identity is evident in the charged N-terminal sequence. SEQ ID NO:6, 7, 8, and 9 are shown in FIG. 1 in a multiple protein alignment. Identical and conserved amino acids are marked in the consensus sequence with "!" and "*," respectively.

In humans, FDC-SP is encoded by a single-copy coding region that maps to chromosome 4q13. The FDC-SP coding region is spread over 10 kb and contains five exons which encode the 5' untranslated region (exon 1), the leader peptide (exon 2), most of the N-terminal charged region (exon 3), the remainder of the coding sequence (exon 4), and the 3' untranslated sequence (exon 5) (see Marshall et al., 2002, J. Immunol., 169:2381-2389). The mouse FDC-SP coding sequence maps to chromosome 5E1. An FDC-SP polypeptide may be isolated from an animal, such as a human, chimpanzee, mouse, or rat. For instance, a genomic copy of an FDC-SP coding region may be isolated and the exon identified. An mRNA encoding an FDC-SP polypeptide, or a cDNA of such an mRNA, may be isolated. An FDC-SP polypeptide may be produced using recombinant techniques, or chemically or enzymatically synthesized using routine methods.

The amino acid sequence of an FDC-SP polypeptide having sequence similarity to SEQ ID NO:2, 3, 4, and/or 5, or a subset of consecutive amino acids chosen from SEQ ID NO:2, 3, 4, or 5 provided the subset includes SEQ ID NO:1, may include conservative substitutions of the corresponding amino acids present in SEQ ID NO: 2, 3, 4, and/or 5. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: H is, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids. SEQ ID NO:6, 7, 8, and 9 are shown in FIG. 1 in a multiple protein alignment. Identical and conserved amino acids are marked in the consensus sequence with "!" and "*," respectively.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

A polypeptide of the present invention having immuno-regulatory activity inhibits IgA production by B cells in vitro. Whether a polypeptide has immuno-modulatory activity may be determined by in vitro assays. An example of an in vitro assay is described in Example 1. The assay uses B cells, which in one embodiment may be a primary cell obtained from an animal, such as a mouse or human, or in another embodiment may be a B cell line. When obtained from an animal, B cells may be obtained from lymphoid tissues such as spleen, tonsil, and lymph node. In one embodiment, the assay includes depleting most (at least 95%) secretory IgA$^+$ (sIgA$^+$) B cells, stimulating the IgA-depleted B cells with either LPS and IL-5 or with TGF-b1 and IL5, for 2 hours, adding an FDC-SP polypeptide at concentrations between 0.5 micromolar and 2 micromolar to the medium, and incubating for 5 days. Supernatants may then be harvested and tested to determine the levels of IgA. In one embodiment, a polypeptide is considered to have immuno-modulatory activity if there is a statistically significant decrease in IgA concentration compared to a control not exposed to the FDC-SP polypeptide. In one embodiment, a polypeptide is considered to have immuno-modulatory activity if there is a decrease in IgA concentration of at least 10%, at least 20%, at least 30%, at least 40%, at least 50%, at least 60%, at least 70%, or at least 80% compared to a control not exposed to the FDC-SP polypeptide.

In one embodiment a polypeptide of the present invention having immuno-modulatory activity inhibits IgA production by B cells in vivo. In one embodiment, an example of an in vivo assay is administration of a polypeptide of the present invention to a mouse, such as an FDC-SP KO mouse (see Example 1). A polypeptide is considered to have immuno-modulatory activity if there is a statistically significant decrease in IgA levels in the mouse, for instance, in broncho-alveolar fluid, compared to a control mouse. In another embodiment, a polypeptide is considered to have immuno-modulatory activity if there is a significant reduction in IgA-related kidney pathology compared to a control mouse.

A polypeptide of the present invention may be expressed as a fusion that includes an additional amino acid sequence not normally or naturally associated with the polypeptide. In one embodiment, the additional amino acid sequence may be useful for purification of the fusion polypeptide by affinity chromatography. Various methods are available for the addition of such affinity purification moieties to proteins. Representative examples include, for instance, polyhistidine-tag (His-tag) and maltose-binding protein (see, for instance, Hopp et al. (U.S. Pat. No. 4,703,004), Hopp et al. (U.S. Pat. No. 4,782,137), Sgarlato (U.S. Pat. No. 5,935,824), and Sharma (U.S. Pat. No. 5,594,115)). In one embodiment, the additional amino acid sequence may be a carrier polypeptide. The carrier polypeptide may be used to increase the immunogenicity of the fusion polypeptide to increase production of antibodies that specifically bind to a polypeptide of the invention. The invention is not limited by the types of carrier polypeptides that may be used to create fusion polypeptides. Examples of carrier polypeptides include, but are not limited to, keyhole limpet hemacyanin, bovine serum albumin, ovalbumin, mouse serum albumin, rabbit serum albumin, and the like. In another embodiment, the additional amino acid sequence may be a fluorescent polypeptide (e.g., green, yellow, blue, or red fluorescent proteins) or other amino acid sequences that can be detected in a cell, for instance, a cultured cell, or a tissue sample that has been removed from an animal. If a polypeptide of the present invention includes an additional amino acid sequence not normally or naturally associated with the polypeptide, the additional amino acids are not considered when percent structural similarity to a reference amino acid sequence is determined.

Polypeptides of the present invention can be produced using recombinant DNA techniques, such as an expression vector present in a cell. Such methods are routine and known in the art. The polypeptides may also be synthesized in vitro, e.g., by solid phase peptide synthetic methods. The solid phase peptide synthetic methods are routine and known in the art. A polypeptide produced using recombinant techniques or by solid phase peptide synthetic methods can be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity The present invention also includes polynucleotides. In one embodiment, a polynucleotide encodes a polypeptide described herein. Also included are the complements of such polynucleotide sequences. A person of ordinary skill can easily determine a polynucleotide sequence encoding a polypeptide described herein by reference to the standard genetic code. A polynucleotide encoding a polypeptide having immuno-modulatory activity is referred to herein as an FDC-SP polynucleotide. In one embodiment, FDC-SP polynucleotides may have a nucleotide sequence encoding a polypeptide having the amino acid sequence shown in SEQ ID NO:4. An example of the class of nucleotide sequences encoding such a polypeptide is SEQ ID NO:10. It should be understood that a polynucleotide encoding an FDC-SP polypeptide represented by SEQ ID NO:4 is not limited to the nucleotide sequence disclosed at SEQ ID NO:10, but also includes the class of polynucleotides encoding such polypeptides as a result of the degeneracy of the genetic code. For example, the naturally occurring nucleotide sequence SEQ ID NO:10 is but one member of the class of nucleotide sequences encoding a polypeptide having the amino acid sequence SEQ ID NO:4. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid.

An FDC-SP polynucleotide of the present invention may further include heterologous nucleotides flanking the open reading frame encoding the FDC-SP polynucleotide. Typically, heterologous nucleotides may be at the 5' end of the coding region, at the 3' end of the coding region, or the combination thereof. The number of heterologous nucleotides may be, for instance, at least 10, at least 100, or at least 1000.

The present invention also includes antibodies that specifically bind a polypeptide of the present invention. In one embodiment, an antibody specifically binds amino acids 60-65 of SEQ ID NO:6, amino acids 56-61 of SEQ ID NO:7, amino acids 59-64 of SEQ ID NO:8, and/or amino acids 59-64 of SEQ ID NO:9. In one embodiment, a short polypeptide may be coupled to a carrier polypeptide to increase immunogenicity, and an adjuvant may be used to also increase immunogenicity. In one embodiment, an antibody specifically binds amino acids 34-65 of SEQ ID NO:6, amino acids 60-84 of SEQ ID NO:6, amino acids 35-64 or SEQ ID NO:8, and/or amino acids 59-85 of SEQ ID NO:8.

Antibody may be produced using a polypeptide described herein. The antibody may be polyclonal or monoclonal. Laboratory methods for producing, characterizing, and optionally isolating polyclonal and monoclonal antibodies are known in the art (see, for instance, Harlow E. et al., 1988, Antibodies: A laboratory manual, Cold Spring Harbor Laboratory Press, Cold Spring Harbor). For instance, a polypeptide of the present invention may be administered to an animal, such as a mammal or a chicken, in an amount effective to cause the production of antibody specific for the administered polypeptide. Optionally, a polypeptide may be mixed with an adjuvant, for instance Freund's incomplete adjuvant, to stimulate the production of antibodies upon administration.

Antibody fragments include at least a portion of the variable region of an antibody that specifically binds to its target. Examples of antibody fragments include, for instance, scFv, Fab, F(ab')$_2$, Fv, a single chain variable region, and the like. Fragments of intact molecules can be generated using methods well known in the art and include enzymatic digestion and recombinant means.

An antibody of the present invention may be coupled (also referred to as conjugated) to a detectable label, e.g., a molecule that is easily detected by various methods. Examples include, but are not limited to, radioactive elements; enzymes (such as horseradish peroxidase, alkaline phosphatase, and the like); fluorescent, phosphorescent, and chemiluminescent dyes; latex and magnetic particles; cofactors (such as biotin); dye crystallites, gold, silver, and selenium colloidal particles; metal chelates; coenzymes; electroactive groups; oligonucleotides, stable radicals, and others. Methods for conjugating a detectable label to antibody vary with the type of label, and such methods are known and routinely used by the person skilled in the art.

The present invention is also directed to compositions including one or more polypeptides described herein. Such compositions typically include a pharmaceutically acceptable carrier. As used herein "pharmaceutically acceptable carrier" includes, but is not limited to, saline, solvents, dispersion media, coatings, antibacterial and antifungal agents, isotonic and absorption delaying agents, and the like, compatible with pharmaceutical administration. Additional active compounds can also be incorporated into the compositions.

A composition may be prepared by methods well known in the art of pharmacy. In general, a composition can be formulated to be compatible with its intended route of administration. Administration may be systemic or local. In some aspects local administration may have advantages for site-specific, targeted disease management. Local therapies may provide high, clinically effective concentrations directly to the treatment site, with less likelihood of causing systemic side effects.

Examples of routes of administration include parenteral, e.g., intravenous, intradermal, subcutaneous, oral, transdermal (topical), and transmucosal administration. In one embodiment, administration may include use of a delivery tool, such as a syringe, for direct injection into a specific site (e.g., during surgery) or by catheter.

Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline. A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (e.g., a polypeptide described herein) in the required amount in an appropriate solvent with one or a combination of ingredients such as those enumerated above, as required, followed by filtered sterilization. Generally, dispersions are prepared by incorporating the active compound into a sterile vehicle, which contains a dispersion medium and other ingredients such as from those enumerated above. In the case of sterile powders for the preparation of sterile injectable solutions, methods of preparation that may be used include vacuum drying and freeze-drying which yields a powder of the active ingredient plus any additional desired ingredient from a previously sterile-filtered solution thereof.

Oral compositions may include an inert diluent or an edible carrier. For the purpose of oral therapeutic administration, the active compound can be incorporated with excipients and used in the form of tablets, troches, or capsules. Oral compositions can also be prepared using a fluid carrier. Pharmaceutically compatible binding agents can be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active compounds may be delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds may be formulated into ointments, salves, gels, or creams as generally known in the art. An example of transdermal administration includes iontophoretic delivery to the dermis or to other relevant tissues.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially. Liposomal suspensions can also be used as pharmaceutically acceptable carriers. These can be prepared according to methods known to those skilled in the art. Delivery reagents such as lipids, cationic lipids, phospholipids, liposomes, and microencapsulation may also be used.

In one embodiment, an active compound may be associated with a targeting group. As used herein, a "targeting group" refers to a chemical species that interacts, either directly or indirectly, with the surface of a cell, for instance with a molecule present on the surface of a cell, e.g., a receptor. The interaction can be, for instance, an ionic bond, a hydrogen bond, a Van der Waals force, or a combination thereof. Examples of targeting groups include, for instance, saccharides, polypeptides (including hormones), polynucleotides, fatty acids, and catecholamines. Another example of a targeting group is an antibody. The interaction between the targeting group and a molecule present on the surface of a cell, e.g., a receptor, may result in the uptake of the targeting group and associated active compound. For instance, B cell-specific antigens may be used, such as, but not limited to, CD19, CD20, CD21, CD22, CD23, surface immunoglobulin, Ig-alpha, and Ig-beta.

When a polynucleotide is introduced into cells using any suitable technique, the polynucleotide may be delivered into the cells by, for example, transfection or transduction procedures. Transfection and transduction refer to the acquisition by a cell of new genetic material by incorporation of added polynucleotides. Transfection can occur by physical or chemical methods. Many transfection techniques are known to those of ordinary skill in the art including, without limitation, calcium phosphate DNA co-precipitation, DEAE-dextrin DNA transfection, electroporation, naked plasmid adsorption, cationic liposome-mediated transfection (commonly known as lipofection). Transduction refers to the process of transferring nucleic acid into a cell using a DNA or RNA virus.

Transgenic mice expressing increased levels of FDC-SP polypeptide showed no evidence of toxicity associated with the polypeptide, and it is expected that administration of an FDC-SP polypeptide to an animal will not be toxic. Toxicity and therapeutic efficacy of such active compounds can be determined by standard pharmaceutical procedures in cell cultures or experimental animals, e.g., for determining the $ED_{50}$ (the dose therapeutically effective in 50% of the population).

The data obtained from cell culture assays and animal studies can be used in formulating a range of dosage for use in humans. The dosage of such active compounds lies preferably within a range of circulating concentrations that include the $ED_{50}$ with little or no toxicity. The dosage may vary within this range depending upon the dosage form employed and the route of administration utilized. For a compound used in the methods of the invention, it may be possible to estimate the therapeutically effective dose initially from cell culture assays. A dose may be formulated in animal models to achieve a circulating plasma concentration range that includes the $IC_{50}$ (i.e., the concentration of the test compound which achieves a half-maximal inhibition of signs and/or symptoms) as determined in cell culture. Such information can be used to more accurately determine useful doses in humans.

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a polynucleotide or a polypeptide can include a single treatment or can include a series of treatments.

Provided herein are animals with decreased FDC-SP expression. Such animals exhibit pathophysiological features of IgA nephropathy including one or more of IgA deposition in kidneys, mesangial hyperproliferation, polypeptide deposition in glomeruli, increased proteinurea, and increased hematuria. Such animals exhibit other characteristics including, but limited to, elevated IgA in serum, saliva and/or bronchoalveolar lavage fluid, and increased IgA expressing B lymphocytes in circulation and several lymphoid tissues. Specific cells of such animals may exhibit decreased FDC-SP expression, including, but not limited to, follicular dendritic cells, monocytes, and/or macrophages. Animals of any species, including, but not limited to, mice, rats, rabbits, and primates, e.g., baboons, monkeys, chimpanzees, and humans may be used to generate an animal with decreased FDC-SP expression.

In one embodiment, an animal with decreased FDC-SP expression is a transgenic animal. A "transgenic animal" is an animal containing one or more cells bearing genetic information received, directly or indirectly, by deliberate genetic manipulation or by inheritance from a manipulated progenitor, such as by microinjection or infection with a recombinant viral vector. This introduced polynucleotide may be integrated within a chromosome. In one embodiment, the introduced polynucleotide is integrated into an FDC-SP locus. A transgenic animal is a non-human animal.

In another embodiment, an animal with decreased FDC-SP expression is an animal administered a polynucleotide, such as an siRNA, that decreases expression of FDC-SP.

A transgenic animal of the present invention can be broadly categorized as a "knock-out." A "knock-out" has a disruption in the target coding region via the introduction of a transgene that results in a decrease of function of the target coding region. A disruption in a target coding region is one that has been mutated using homologous recombination or other approaches known in the art. A disrupted coding sequence can be either a hypomorphic allele of the coding sequence or a null allele of the coding sequence. The term "transgene" refers to a polynucleotide, which is partly or entirely heterologous, i.e., foreign, to the transgenic animal or cell into which it is introduced, or, is homologous to an endogenous gene of the transgenic animal or cell into which it is introduced, but which is designed to be inserted into the animal's genome in such a way as to alter the genome of the cell into which it is inserted (e.g., its insertion results in a knockout). For example, a transgene may be directed to disrupting one or more FDC-SP coding regions by homologous recombination with genomic sequences of an FDC-SP coding region.

In one embodiment, expression of the target coding region is insignificant or undetectable. In one embodiment, expression of the target coding region is decreased by at least 40%, at least 60%, at least 80%, or at least 90% compared to a control animal. A knock-out transgenic animal can be heterozygous or homozygous with respect to a disrupted target coding region.

A transgenic animal of the present invention includes one that carries heterozygous or homozygous knock out in all their cells, as well as animals which carry heterozygous or homozygous knock out in some, but not all their cells, i.e., mosaic animals. Also provided herein are cells and tissues from a transgenic animal of the present invention.

Coding sequences may be altered in many types of animals. Targeting of a coding region involves the use of standard recombinant DNA techniques to introduce a desired mutation into a cloned polynucleotide of a chosen locus, e.g., a polynucleotide having a nucleotide sequence derived from an FDC-SP coding region. That mutation is then transferred through homologous recombination to the genome of a pluripotent, embryo-derived stem (ES) cell. The altered stem cells are microinjected into mouse blastocysts and are incorporated into the developing mouse embryo to ultimately develop into chimeric animals. In some cases, germ line cells of the chimeric animals will be derived from the genetically altered ES cells, and the mutant genotypes can be transmitted through breeding.

In order to target a coding region, the coding region of interest may be cloned and modified to result in a disruption when it is inserted into a target coding region by homologous recombination. A cloned coding region may be modified to include a polynucleotide encoding a selectable marker. A selectable marker is useful for selecting stable transformants in culture, and example include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Optionally, a sequence encoding a selectable marker can be flanked by recognition sequences for a recombinase such as, e.g., Cre or Flp. For example, a selectable marker can be flanked by loxP recognition sites (34 by recognition sites recognized by the Cre recombinase) or FRT recognition sites such that the selectable marker can be excised from the construct (Orban, et al., 1992, Proc. Natl. Acad. Sci. USA, 89:6861-6865, Brand and Dymecki, 2004, Dev. Cell., 6:7-28). Crossing the transgenic animal with another animal expressing Cre or Flp can result in excision of the nucleotides between the recognition sites to result in a knock out. Thus, this technology results in the gross destruction of the coding region of interest.

Methods for making transgenic animals are known in the art and are routine. The transgenic animal cells of the present invention may be prepared by introducing one or more DNA molecules into a cell, which may be a precursor pluripotent cell, such as an ES cell, or equivalent (Robertson, E. J., In: Current Communications in Molecular Biology, Capecchi, M. R. (ed.), Cold Spring Harbor Press, Cold Spring Harbor, N.Y. (1989), pp. 39-44). The term "precursor" is intended to denote only that the pluripotent cell is a precursor to the desired ("transfected") pluripotent cell. The pluripotent (precursor or transfected) cell can be cultured in vivo in a manner known in the art (Evans, M. J. et al., Nature 292:154-156 (1981)) to form a chimeric or transgenic animal.

An animal with decreased FDC-SP expression may be an animal administered a polynucleotide, such as an siRNA, that decreases expression of FDC-SP. Decreasing expression of an FDC-SP coding region may be accomplished by using a portion of a polynucleotide described herein. In one embodiment, a polynucleotide for decreasing expression of an FDC-SP coding region in a cell includes one strand, referred to herein as the sense strand, of at least 19 nucleotides, for instance, 19, 20, 21, 22, 23, 24, 25, 26, 27, 28, or 29 nucleotides (e.g., lengths useful for dsRNAi and/or antisense RNA). The sense strand is substantially identical, preferably, identical, to a target coding region or a target mRNA. As used herein, the term "identical" means the nucleotide sequence of the sense strand has the same nucleotide sequence as a portion of the target coding region or the target mRNA. As used herein, the term "substantially identical" means the sequence of the sense strand differs from the sequence of a target mRNA at least 1%, 2%, 3%, 4%, or 5% of the nucleotides, and the remaining nucleotides are identical to the sequence of the mRNA.

In one embodiment, a polynucleotide for decreasing expression of an FDC-SP coding region in a cell includes one strand, referred to herein as the antisense strand. The antisense strand may be at least 19 nucleotides, for instance, 19, 20, 21, 22, 23, 24, 25, 26, 27, 28, or 29 nucleotides. In one embodiment, a polynucleotide for decreasing expression of an FDC-SP coding region in a cell includes substantially all of a coding region, or in some cases, an entire coding region. An antisense strand is substantially complementary, preferably, complementary, to a target coding region or a target mRNA. As used herein, the term "substantially complementary" means that at least 1%, 2%, 3%, 4%, or 5% of the nucleotides of the antisense strand are not complementary to a nucleotide sequence of a target coding region or a target mRNA.

The present invention includes methods for using the polypeptides disclosed herein. In one embodiment, the methods include administering to a subject an effective amount of a polypeptide described herein. The subject can be, for instance, a member of the family Muridae (a murine animal such as rat or mouse), or a primate, such as a human.

In one embodiment, the methods may include decreasing IgA concentration in a subject. In this aspect of the invention, an "effective amount" is an amount effective to result in a decrease of in the IgA concentration in a subject. Without intending to be limited by theory, the method may result in inhibition of IgA production by the subject's B cells, and/or the method may result in inhibition of generation of IgA producing B cells.

The decrease of IgA concentration may be in any tissue or fluid of the subject. For example, an IgA concentration may be decreased in the subject's serum, bronchoalveolar lavage fluid, saliva, gut, or a combination thereof. The decrease in IgA concentration does not require a decrease in all tissues and fluids of a subject. For instance, the IgA concentration may decrease in a subject's serum but not in the subject's saliva. In one embodiment, the decrease in IgA concentration may be a decrease of at least 10%, at least 20%, at least 30%, at least 40%, at least 50%, at least 60%, at least 70%, or at least 80% compared to the IgA concentration in the same tissue or fluid of the subject before the administration. Methods for determining the concentration of IgA in a tissue or fluid are known in the art and routine.

The present invention also includes methods of treating certain diseases in a subject. The subject may be a mammal, including members of the family Muridae (a murine animal such as rat or mouse), or a primate, such as a human. As used herein, the term "disease" refers to any deviation from or interruption of the normal structure or function of a part, organ, or system, or combination thereof, of a subject that is manifested by a characteristic sign or set of signs. As used herein, the term "sign" refers to objective evidence of a disease present in a subject. Signs associated with diseases referred to herein and the evaluation of such signs is routine and known in the art. Diseases include conditions associated with excessive IgA production. Examples of such conditions include, but are not limited to, IgA nephropathy, Henoch-Schönlein purpura, and IgA pemphigus. Typically, whether a subject has a disease, and whether a subject is responding to treatment, may be determined by evaluation of signs associated with the disease. For instance, signs of IgA nephropathy include hematuria, elevated levels of circulating IgA-fibronectin complex, and granular deposition of IgA and C3 in a widened renal mesangium, with foci of segmental proliferative or necrotizing lesions.

Treatment of a disease can be prophylactic or, alternatively, can be initiated after the development of a disease. Treatment that is prophylactic, for instance, initiated before a subject manifests signs of a disease, is referred to herein as treatment of a subject that is "at risk" of developing a disease. An example of a subject that is at risk of developing a disease is a person having a risk factor. Risk factors for one disease, IgA nephropathy, are thought to include activation of mucosal defenses by, for instance, immunization, and geographical location, where IgA nephropathy is the most common glomerular disease in the Far East (including China, Japan, and South Korea) and Southeast Asia (including Philippines, Singapore, and Thailand). Treatment can be performed before, during, or after the occurrence of the diseases described herein. Treatment initiated after the development of a disease may result in decreasing the severity of the signs of the disease, or completely removing the signs.

In some aspects, the methods typically include administering to the subject an effective amount of an FDC-SP polypeptide, The subject may have symptoms of a disease that includes excessive IgA production. As used herein, an "effective amount" is an amount effective to inhibit decrease IgA levels in a subject, decrease signs associated with a disease, or the combination thereof. Whether a polypeptide is expected to function in methods of the present invention relating to treatment can be evaluated using the animal model described herein.

Another method of the present invention includes contacting a cell with a polypeptide described herein. The cell may be ex vivo. The cell may be a B cell, a T cell, or dendritic cell. Examples of B cells includes plasma B cells, memory B cells, B-2 cells, marginal zone B cells, and follicular B cells. The cells may be animal cells, such as vertebrate cells, including murine (rat or mouse), or primate cells, such as human cells. In one embodiment the cells may be obtained from, for instance, spleen, primary lymph node, secondary lymph node, or plasma. Other examples of animals from which cells may be obtained include a transgenic animal that expresses increased amounts of FDC-SP and an animal described herein that expresses decreased amounts of FDC-SP. In one embodiment, cell lines may be used. Examples of such cell lines may include FDC-1 cells, BK cells, or L cells containing an FDC-SP expression vector or induced to express FDC-SP using TNF-alpha. In one embodiment, such as when the cells are B cells, the cells are first induced with either LPS and IL-5 or with TGF-b1 and IL5. In one embodiment, for instance when the cell is a B cell, the contacting may result in decreasing IgA production by the B cells, and/or inhibition of generation of IgA producing B cells.

The methods of the present invention can include administering to a subject having a disease or at risk of developing a disease a composition including an effective amount of a polypeptide of the present invention, wherein the concentration of IgA in a tissue and/or fluid is decreased, a sign associated with the disease is decreased, or a combination thereof. Methods for administering a polypeptide of the present invention include, but are not limited to, oral, respiratory, and/or parenteral administration.

The polynucleotides of the present invention can also be administered to a subject in combination with other therapeutic compounds to increase the overall therapeutic effect. Therapeutic compounds useful for the treatment of the diseases described herein are known and used routinely. Agents for treating diseases described herein are available that may be used as a second, supplemental agent, to complement the activity of the polypeptides described herein. Such agents may include, for instance, steroids.

Also included in the present invention are methods for identifying a compound that decreases the production of IgA by a cell. In one embodiment the method includes contacting a cell, such as a B cell, with a compound, incubating the cell and the agent under conditions suitable for culturing the cell, and measuring the production of IgA by the cell. The B cell may be stimulated to produce IgA prior to the contacting, or the B cell may already be producing IgA. For instance, the B cell may constitutively produce IgA or it may be isolated from an animal as an IgA producing B cell. The cell used in the method may be an ex vivo cell, such as a cell line or a cell removed from an animal. The animal may be a wild type animal, or the animal disclosed herein (an animal producing increased amounts of IgA). The cell contacted with the agent having decreased IgA production when compared to IgA production by a corresponding control cell that was not contacted with the compound indicates the compound decreases the production of IgA by the cell. The compound can be, but is not limited to, a chemical compound, including, for instance, an organic compound, an inorganic compound, a metal, a polypeptide, a non-ribosomal polypeptide, a polyketide, or a peptidomimetic compound. The sources for potential compounds to be screened include, for instance, chemical compound libraries, cell extracts of plants and other vegetations.

The present invention also includes methods for using the animal model disclosed herein. As set forth in the Examples, an animal expressing decreased levels of FDC-SP has a phenotype that is characterized by pathophysiological features of IgA nephropathy including one or more of IgA deposition in kidneys, mesangial hyperproliferation, polypeptide deposition in glomeruli, increased proteinurea, and increased hematuria. Such a phenotype is similar to the signs associated with IgA nephropathy in humans.

Thus, the present invention provides a model system that includes the animals disclosed herein, and methods useful in the study of aspects of the etiology of diseases associated with increased levels of IgA, such as IgA nephropathy. The methods are also useful for screening and selecting for compounds that have an effect on diseases associated with increased levels of IgA, such as IgA nephropathy, the further study of these compounds, and the possible administration of selected compounds to humans in order to regulate diseases associated with increased levels of IgA, such as IgA nephropathy.

The present invention is illustrated by the following examples. It is to be understood that the particular examples, materials, amounts, and procedures are to be interpreted broadly in accordance with the scope and spirit of the invention as set forth herein.

Example 1

We have established that mice deficient in the immunomodulatory peptide FDC-SP develop the features of IgA nephropathy (IgAN). FDC-SP KO mice develop up to 10 fold elevation of IgA in serum, saliva and bronchoalveolar lavage fluid. IgA expressing B lymphocytes are significantly increased in circulation and several lymphoid tissues and isolated B lymphocytes show enhanced IgA production in vitro. These mice show evidence of IgA deposition in kidneys and moderate kidney pathology, characterized by mesangial hyperproliferation and protein deposition in some glomeruli. Serum creatinine and urea levels are within normal levels consistent with chronic kidney dysfunction rather than acute severe injury.

Materials and Methods

FDC-SP-Deficient and Transgenic Mice

FDC-SP-deficient mice were generated by Biogen-Idec using the targeting construct illustrated in FIG. 2. The construct was linearized and transfected into 129/Sv ES cells by electroporation. G418 resistant colonies were screened by PCR and Southern blot and a correctly targeted clone was injected into C57BL6 blastocysts, which were then implanted into pseudo-pregnant foster mothers. Chimeric offspring were identified by coat color and bred to assess germline transmission. Pups positive for the targeted FDC-SP allele were crossed with Cre transgenics to generate the collapsed targeted FDC-SP locus. The collapsed locus was transmitted in the germline through subsequent back-crossing to C57BL6 mice, during which the Cre transgene was removed. Homozygous FDC-SP-deficient mice were generated after back-crossing to C57BL6 for 7 generations at University of Manitoba. Mice were genotyped using DNA extracted from ear punches, using the following primers. The wild type allele was amplified with GGGATAAAGTGATAAAAACGAATAGCCA (SEQ ID NO:11) and ACGGAAATCCAGAAGATGCAAGCCT (SEQ ID NO:12) to result in a 430 bp product. The knockout allele was amplified with GGGATAAAGT- GATAAAAACGAATAGCCA (SEQ ID NO:11) and GGAG-GAGTAGAAGGTGGCGCGAAG (SEQ ID NO:13) to result in a 522 bp product.

FDC-SP transgenic CD1 mice (i.e., mice constitutively expressing FDC-SP in lymphoid tissues) were generated as described (Al-Alwan et al., 2007, J. Immunol., 178:7859-7867). All experimental animals were housed at the Central Animal Care Facility (University of Manitoba, Winnipeg, MB) in compliance with the guidelines established by the Canadian Council on Animal Care.

Flow Cytometry Analyses

Single cell suspensions were generated from the indicated tissues and were pre-incubated with hybridoma supernatant containing Fc receptor blocking antibody. The indicated conjugated Abs were added from the following panel: V500-labeled anti-CD4, PE anti-CD5, FITC anti-CD11b, FITC anti-CD21, PE anti-CD23, PerCP anti-CD45R/B220, FITC anti-CD54/B220, PE anti-CD43, PE anti-Gr1 and APC anti-IgM (all BD Biosciences), Pacific Blue anti-CD8, AlexaFluor647 anti-mouse CD4 and PE anti-mouse IgA (eBioscience). Stained cells were washed and acquired on a FACS Canto II flow cytometer (BD Biosciences). Data were analyzed using FlowJo software (TreeStar).

Immunization and Antibody Measurements

Serum, saliva and bronchoalveolar lavage fluid were collected from 10-14 week old FDC-SP-deficient mice, FDC-SP transgenic mice and strain, age and sex-matched controls. Where indicated mice were immunized intraperitoneally with NP-OVA, alum and LPS. For ELISA assays, ninety-six well assay plates were coated overnight at 4° C. with capture antibodies or antigen diluted in carbonate coating buffer (0.015M $Na_2CO_3$, 0.035M $NaHCO_3$, 0.05% $NaN_3$, pH 9.6). Total antibodies levels were determined by coating with anti-mouse IgM or IgA (Jackson ImmunoResearch Laboratories) and NP-specific antibodies levels were determined by coating plates with NP20-BSA (Biosearch Technologies). Detection was carried out using biotinylated anti-mouse IgM or IgA antibodies (Southern Biotechnology) followed by streptavidin alkaline phosphatase.

B Cell Isolation and Cultures

Mouse splenocytes were collected and B cells were purified by negative selection with the CD43 MicroBeads and MACS columns (Miltenyi Biotech). Purified B cells were incubated in dishes coated with goat anti-mouse IgA (4 µg/ml) for 70 min at 4° C., resulting in >95% depletion of $sIgA^+$ cells. IgA-depleted B cells were then washed and resuspended in complete medium (RPMI 1640 containing penicillin-streptomycin, 2-mercaptoethanol and 10% FBS). A total of 4 $10^5$ cells/well were cultured in flat-bottomed, 96-well tissue-culture plates in a volume of 100 µl complete medium containing 10 µg/ml LPS (Escherichia coli 0127:B8; Sigma Chemical Co.), 100 U/ml murine IL-5 (R&D Systems) and 1 ng/ml TGF-β1 (R&D Systems). After 2 hours of culture an additional 100 µl/well of medium containing the indicated FDC-SP peptides was added. After 5 days of culture, supernatants were harvested for ELISA analysis and cells for flow cytometry. FDC-SP containing L cell supernatants were generated from stable transfectants generated as described (Al-Alwan et al., 2007, J. Immunol., 178:7859-7867). Serum-free supernatants were prepared by extensively washing and culturing confluent L cells in medium containing 0.5% BSA overnight. Supernatants were harvested and used immediately or aliquoted and stored frozen at −80° C. Synthetic FDC-SP peptides were purchased from Neo BioScience (Cambridge, Mass.) and were greater than 98% pure.

Urine and Kidney Analyses:

Kidneys were harvested from 8 month old FDC-SP deficient mice and either embedded in O.C.T. compound (Tissue Tek) and snap frozen using liquid nitrogen for cryosectioning or formalin fixed for pathology analyses. Cryosections were cut at 8 µm using a cryostat and placed onto slides (Fisherbrand Superfrost/Plus). Frozen sections were fixed for 15-20 minutes using ice cold acetone, blocked with 10% normal goat serum for 1 hr and stained with FITC anti-IgA (Southern Biotechnology). After mounting, sections were imaged using a confocal microscope (Ultraview LCI, Perkin-Elmer). For pathology analyses, formalin fixed kidneys were paraffin embedded, sectioned and stained with hematoxylin and eosin or periodic acid—Schiff stains. For 24 hour urine protein assay, individual mice were put in a metabolic cage with water but no food for 24 hours. Collected urine was clarified by centrifugation at 3000 rpm and protein measured using Bradford protein assay (Biorad). Total protein was determined by multiplying protein concentration by volume and was independently measured 3 times per animal.

Results

FDC-SP-Deficient (KO) Mice and FDC-SP Transgenic (TG) Mice

Figure 2A:
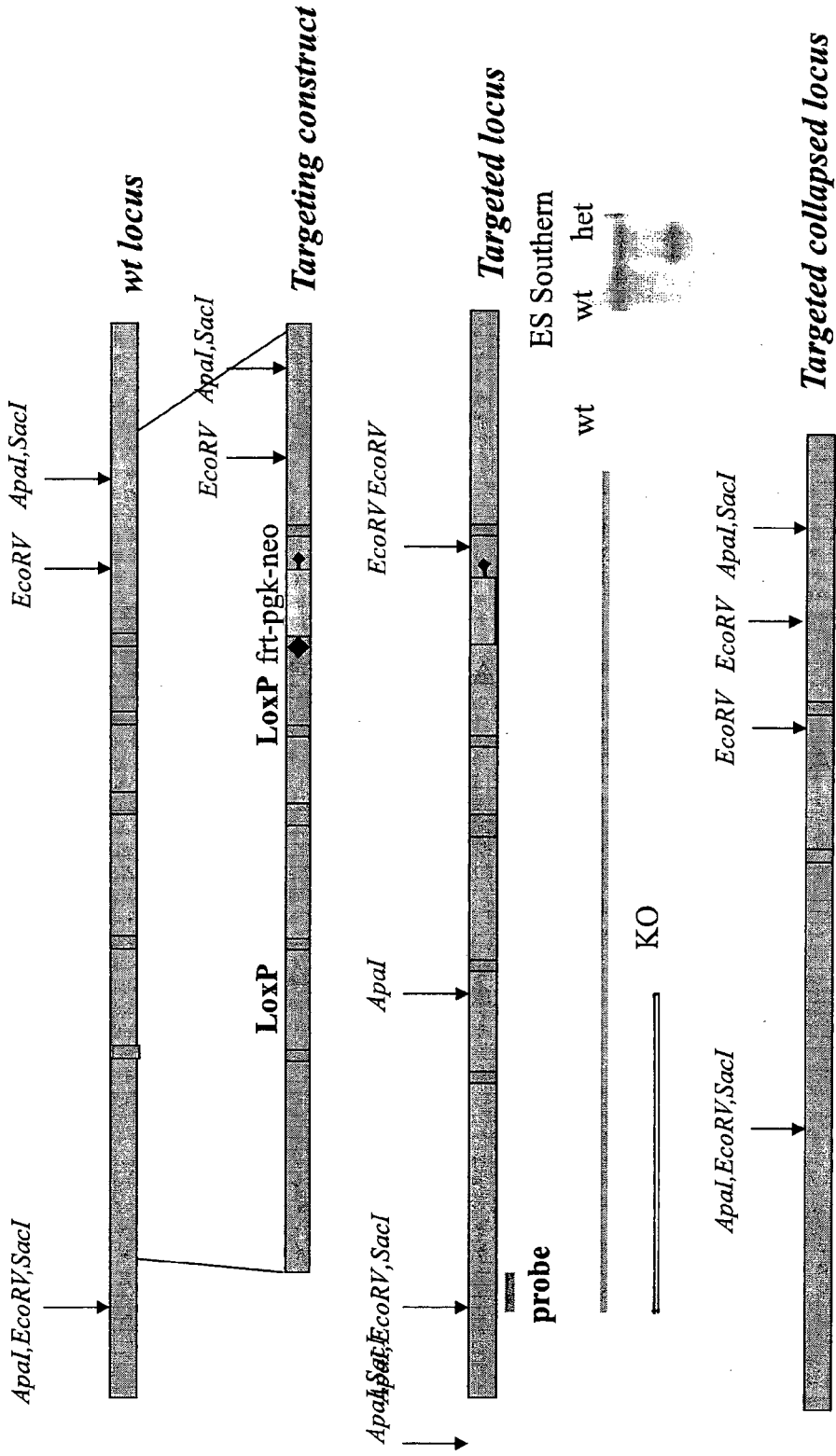
FIG. 2. A; schematic showing strategy for constructing a deletion within the mouse FDC-SP gene removing a coding region encoding an FDC-SP polypeptide (referred to a knockout or KO below).
FIG. 2B. Nucleotide sequence (SEQ ID NO:14) of the gene targeting construct shown in FIG. 2A. The location and sequence of the primer SC3-416 (SEQ ID NO:11), and the location and reverse sequence of the primer SC3-412 (SEQ ID NO:12) and the primer 4R2 (SEQ ID NO:13) are shown. Also shown are the two LoxP sites.

FIG. 1A shows an alignment of FDC-SP protein sequences from mouse, rat, human and chimpanzee. FIG. 1B shows the mouse FDC-SP nucleotide sequence (cDNA). Transgenic mice constitutively expressing FDC-SP in all lymphoid tissues were generated as described in (Al-Alwan et al., 2007, J. Immunol., 178:7859-7867). FIG. 2A illustrates the gene targeting construct used to generate mice devoid of FDC-SP (FDC-SP KO). FIG. 2B represents the nucleotide sequence of the FDC-SP gene targeting construct.

FDC-SP Regulates IgA Production In Vivo

Figure 3:
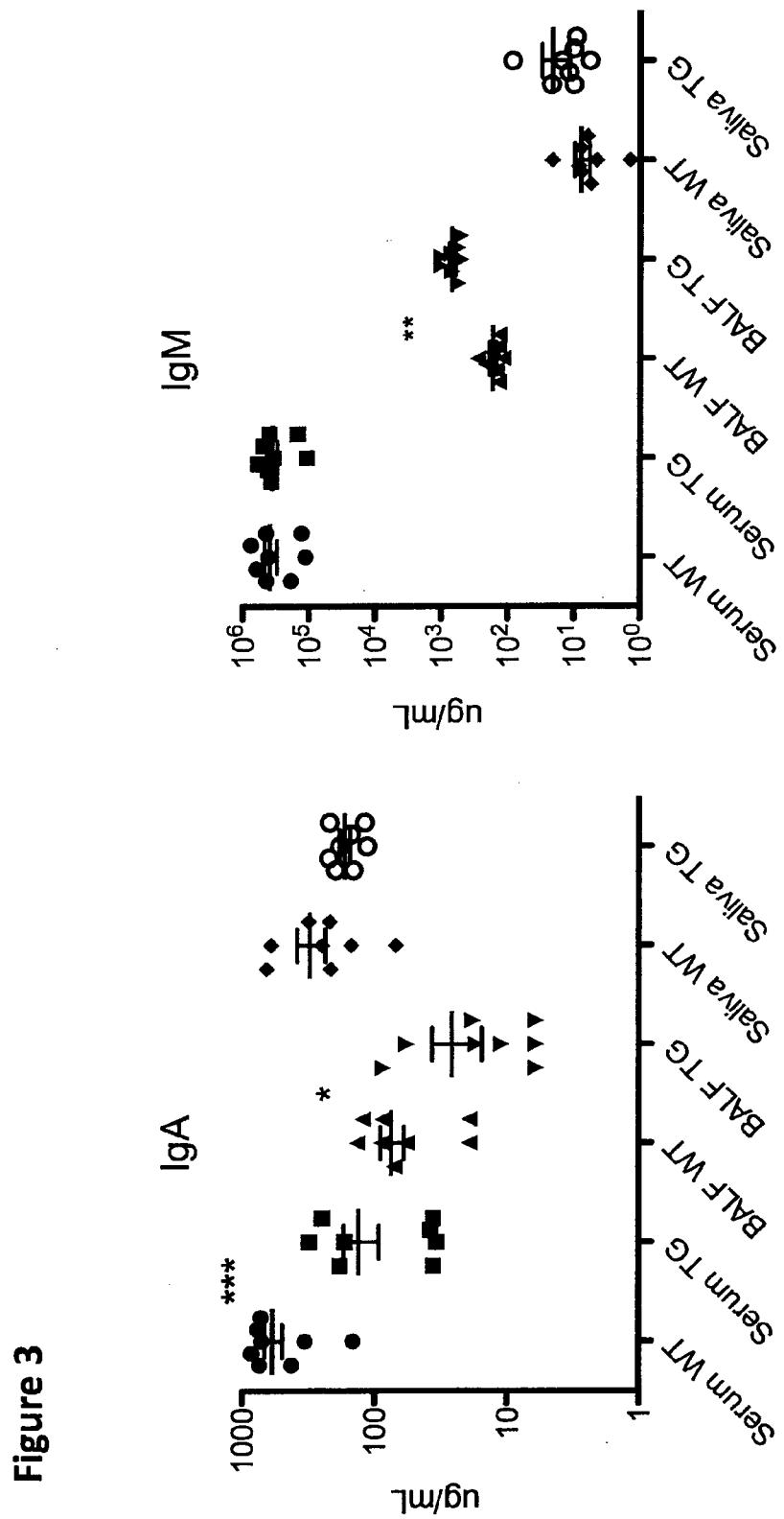
FIG. 3. Saliva was collected from anesthetized 10-14 week old control CD1 mice (WT) or FDC-SP transgenic (TG) mice and then animals were sacrificed by cardiac puncture to collect blood. Bronchoalveolar lavage (BALF) fluid was collected by flushing lungs with 10 mL of PBS. Levels of IgA or IgM antibody isotypes were measured using specific ELISA assays.

As shown in FIG. 3, saliva was collected from anesthetized 10-14 week old control CD1 mice (WT) or FDC-SP transgenic (TG) mice and then animals were sacrificed by cardiac puncture to collect blood. Bronchoalveolar lavage (BALF) fluid was collected by flushing lungs with 10 mL of PBS. Levels of IgA or IgM antibody isotypes were measured using specific ELISA assays. The results show FDC-SP transgenic mice have reduced IgA levels in serum, bronchoalveolar lavage and saliva, whereas IgM levels are not reduced.

Figure 4:
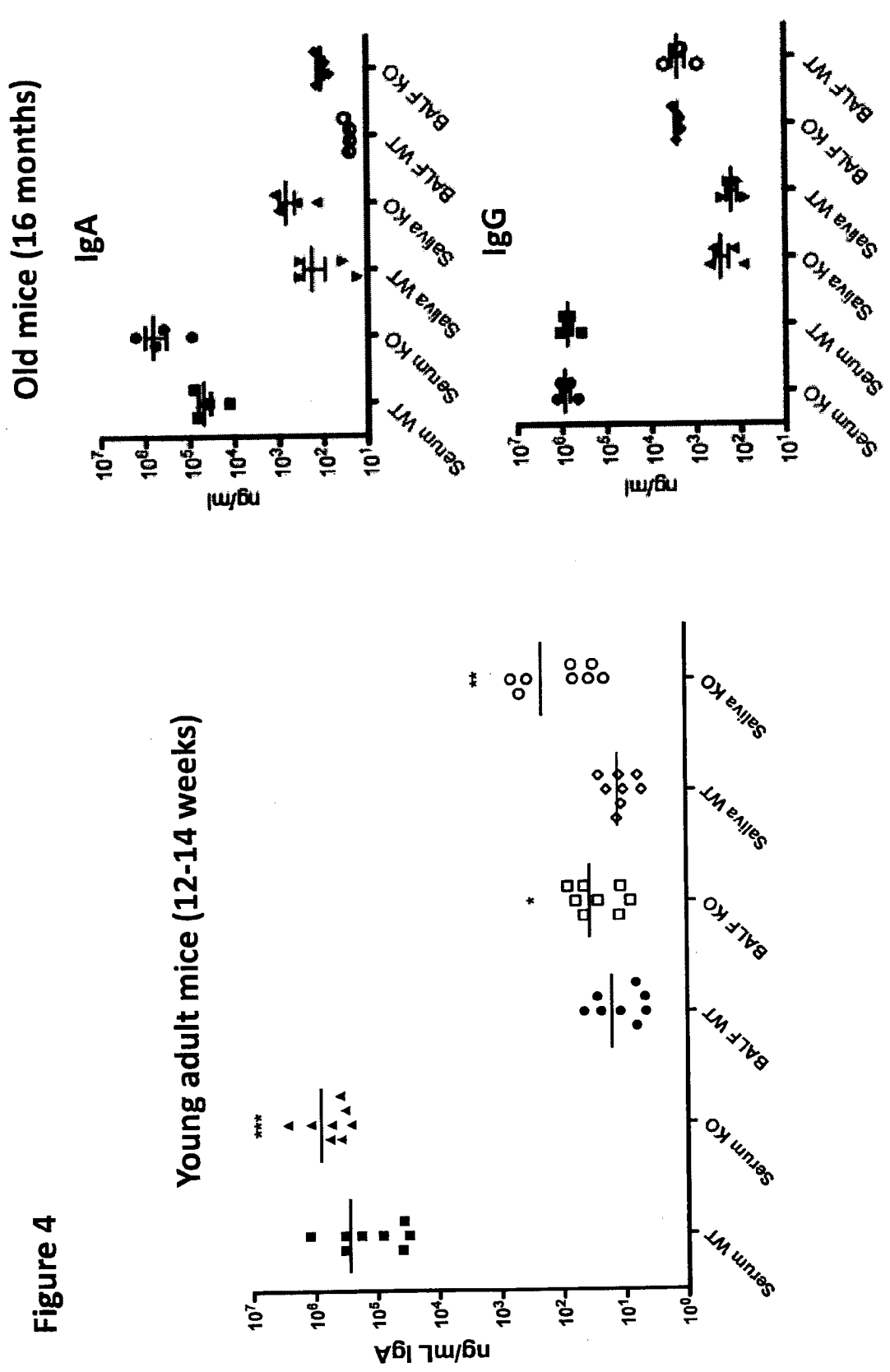
FIG. 4. Saliva was collected from anesthetized 10-14 week old control C57BL6 mice (WT) or FDC-SP knockout (KO) mice generated using the targeting construct in FIG. 2. Animals were sacrificed by cardiac puncture to collect blood.

As shown in FIG. 4, saliva was collected from anesthetized 10-14 week old control C57BL6 mice (WT) or FDC-SP knockout (KO) mice and then animals were sacrificed by cardiac puncture to collect blood. Bronchoalveolar lavage (BALF) fluid was collected by flushing lungs with 10 mL of PBS. Levels of the indicated antibody isotypes were measured using specific ELISA assays. The results show FDC-SP knockout mice have enhanced IgA levels that persist for over one year.

Together the data in FIGS. 3 and 4 indicate that the products of the FDC-SP gene can regulate IgA production in vivo. FDC-SP is not Required for B Lymphocyte Development, but Controls the Generation of IgA+Cells As shown in FIG. 5, lymph node, spleen and blood cells were collected from young adult FDC-SP KO mice and frequency of IgA+B lymphocytes were measured by flow cytometry. Bottom panels represent results from additional flow cytometry analyses which indicate otherwise normal B cell subset composition in FDC-SP KO mice. Graphs represent mean and SEM of 4 mice per genotype. The results show that FDC-SP KO mice have relatively normal B lymphocyte populations but an increased frequency of IgA+B cells.

FDC-SP Derived Peptides can Directly Suppress B Cell IgA Production In Vitro

As shown in FIG. 6, B cells were purified from spleens of control (WT) or FDC-SP KO mice using negative selection with anti-CD43 coupled magnetic beads. Cells were cultured for 5 days with the indicated stimuli, supernatants were harvested and IgA production was assessed by ELISA assays. The results show that B cells isolated from FDC-SP knockout mice generate more IgA when stimulated in vitro.

As shown in FIG. 7, B cells were purified from spleens of control or FDC-SP TG mice using negative selection with anti-CD43 coupled magnetic beads. Cells were cultured for 5 days with the indicated stimuli, supernatants were harvested and IgA production was assessed by ELISA assays. The results show B cells isolated from FDC-SP transgenic mice generate less IgA when stimulated in vitro.

As shown in FIG. 8, B cells were purified from spleens of C57BL6 mice using negative selection with anti-CD43 coupled magnetic beads. Cells were cultured for 5 days with the indicated stimuli and the indicated percentage of a supernatant containing recombinant FDC-SP (FDC-SP SN) or a control supernatant (Control SN). IgA production was assessed by ELISA assays. The results show that addition of recombinant FDC-SP in the form of supernatant of L cells transfected with FDC-SP expression vector suppressed IgA production in vitro.

As shown in FIG. 9, the indicated synthetic peptides P1-P3 corresponding to mouse FDC-SP were purchased and added to cultures of mouse B cells stimulated to produce IgA. The resulting levels of IgA or IgM production were assessed by ELISA assays of culture supernatants. Percentage of cultured cells expressing IgA was also determined by flow cytometry (middle graph). Note that peptide P1 had no effect. Control peptides C1 and C2 are scrambled versions of corresponding FDC-SP derived peptides. The results show portions of FDC-SP have direct inhibitory activity on B cell IgA production in vitro.

As shown in FIG. 10, the effect of the indicated synthetic peptides on IgA or IgM production were assessed by ELISA assays of culture supernatants. Control peptide C5 is a scrambled version of P8. The results show the 6-mer represented by P8 is sufficient to inhibit B cell IgA production in vitro.

Urine and Kidney Analyses Show IgA Nephropathy-Like Disease in FDC-SP KO Mice

As shown in FIG. 11, urine or serum collected from mice greater than one year old were assessed for the indicated biomarkers of kidney dysfunction. The results show significant proteinurea and hematuria in FDC-SP KO mice, indicating chronic nephropathy.

As shown in FIG. 12, kidneys from FDC-SP KO mice were assessed for abnormal histology by staining sections of formalin-fixed kidney with H&E or PAS stain. Abnormal glomeruli with mesangial hypercellularity were noted and glomerular capillary hyaline thrombi were present, indicating protein deposits.

As showed in FIG. 13, further analysis of kidney cryosections stained with FITC-labeled anti-IgA showed evidence of mesangial IgA deposition.

Together these results indicate that the elevated IgA levels in FDC-SP KO mice result in kidney pathology similar to that of IgA nephropathy.

The FDC-SP mouse model offers a tool to dissect the molecular and cellular pathology of IgAN and test new targeted treatments. The available evidence suggests that FDC-SP acts to regulate induction or retention of IgA producing B cells at mucosal sites. The model thus replicates a key aspect of the human disease etiology, where disruption of mucosal B cell regulation is thought to lead to abnormal systemic IgA production. FDC-SP is not normally expressed in kidney tissue, thus this model also facilitates studies focused on the pathology attributable to dysregulated IgA.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for altering IgA concentration in a subject comprising administering to the subject in need thereof an effective amount of an FDC-SP polypeptide, wherein the FDC-SP polypeptide results in a decreased IgA level in the subject compared to the subject before the administration, wherein the subject is a human, and wherein the subject has signs of a disorder that comprises excessive IgA production, wherein the disorder is glomerulonephritis, IgA pemphigus, or a combination thereof, wherein the glomerulonephritis is IgA nephropathy, Henoch-Schönlein purpura, or a combination thereof.

2. The method of claim 1 wherein the IgA level is decreased in serum, in bronchoalveolar lavage fluid, in saliva, or a combination thereof.

3. The method of claim 1 wherein the method further comprises identifying a subject having or at risk of an IgA mediated condition.

4. The method of claim 1 wherein the FDC-SP polypeptide comprises an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 80% amino acid similarity with SEQ ID NO:2 or SEQ ID NO:4.

5. The method of claim 1 wherein the FDC-SP polypeptide comprises an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 80% amino acid similarity with a subset of consecutive amino acids chosen from SEQ ID NO:2 or 4.

6. The method of claim 1 wherein the decrease is a decrease of at least 10% compared to the IgA level in the same tissue or fluid of the subject before the administration.

7. A method for treating a subject comprising:
administering to the subject an effective amount of an FDC-SP polypeptide, wherein the subject has signs of a disorder that comprises excessive IgA production, wherein the disorder comprises a glomerulonephritis, IgA pemphigus, or a combination thereof, wherein the subject is a human.

8. The method of claim 7 wherein the glomerulonephritis is selected from IgA nephropathy and Henoch-Schönlein purpura.

9. A method for treating a subject comprising:
administering to the subject an effective amount of an FDC-SP polypeptide, wherein the subject has signs of a disorder that comprises excessive IgA production, wherein the disorder comprises IgA pemphigus.

10. The method of claim 1 wherein the FDC-SP polypeptide comprises an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide comprises no greater than 31 amino acids and has at least 80% amino acid similarity with amino acids 35-64 of SEQ ID NO:8.

11. The method of claim 1 wherein the polypeptide comprises an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the isolated polypeptide comprises no greater than 25 amino acids and has at least 80% amino acid similarity with amino acids 59-85 of SEQ ID NO:8.

12. The method of claim 7 wherein the FDC-SP polypeptide comprises an amino acid sequence $X_1X_2X_3PWX_4$ (SEQ ID NO:1), wherein $X_1$ and $X_2$ are any amino acid, $X_3$ is Y, F, or N, and $X_4$ is Y or F.

13. The method of claim 7 wherein the FDC-SP polypeptide comprises an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 80% amino acid similarity with SEQ ID NO:2 or SEQ ID NO:4.

14. The method of claim 7 wherein the FDC-SP polypeptide comprises an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide has at least 80% amino acid similarity with a subset of consecutive amino acids chosen from SEQ ID NO:2 or 4.

15. The method of claim 7 wherein the FDC-SP polypeptide comprises an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the amino acid sequence of the isolated polypeptide comprises no greater than 31 amino acids and has at least 80% amino acid similarity with amino acids 35-64 of SEQ ID NO:8.

16. The method of claim 7 wherein the polypeptide comprises an amino acid sequence $X_1X_2X_3PWX_4$ (SEQ ID NO:1), wherein $X_1$ and $X_2$ are any amino acid, $X_3$ is Y, F, or N, and $X_4$ is Y or F, and wherein the isolated polypeptide comprises no greater than 25 amino acids and has at least 80% amino acid similarity with amino acids 59-85 of SEQ ID NO:8.

17. The method of claim 7 wherein the administering results in a decreased IgA level in the subject compared to the subject before the administering.

18. The method of claim 17 wherein the decreased IgA level is a decrease of at least 10% compared to the IgA concentration in the same tissue or fluid of the subject before the administration.

19. The method of claim 17 wherein the IgA level is decreased in serum, in bronchoalveolar lavage fluid, in saliva, or a combination thereof.

* * * * *

UNITED STATES PATENT AND TRADEMARK OFFICE
CERTIFICATE OF CORRECTION

PATENT NO. : 9,339,526 B2
APPLICATION NO. : 13/979887
DATED : May 17, 2016
INVENTOR(S) : Aaron Marshall and Sen Hou Page 1 of 1

It is certified that error appears in the above-identified patent and that said Letters Patent is hereby corrected as shown below:

In the specification,

Column 2, line (10), "SEQ 11)" should be --SEQ ID--

Signed and Sealed this
Twenty-sixth Day of July, 2016

Michelle K. Lee
*Director of the United States Patent and Trademark Office*

SEQUENCE LISTING

<160> NUMBER OF SEQ ID NOS: 14

<210> SEQ ID NO 1
<211> LENGTH: 6
<212> TYPE: PRT

```
<213> ORGANISM: artificial
<220> FEATURE:
<223> OTHER INFORMATION: FDC-SP polypeptide
<220> FEATURE:
<221> NAME/KEY: MISC_FEATURE
<222> LOCATION: (1)..(1)
<223> OTHER INFORMATION: the amino acid at position 1 may be any amino
      acid
<220> FEATURE:
<221> NAME/KEY: MISC_FEATURE
<222> LOCATION: (2)..(2)
<223> OTHER INFORMATION: the amino acid at position 2 may be any amino
      acid
<220> FEATURE:
<221> NAME/KEY: MISC_FEATURE
<222> LOCATION: (3)..(3)
<223> OTHER INFORMATION: the amino acid at position 3 may be tyrosine,
      phenylalanine, or asparagine
<220> FEATURE:
<221> NAME/KEY: MISC_FEATURE
<222> LOCATION: (6)..(6)
<223> OTHER INFORMATION: the amino acid at position 6 may be tyrosine or
      phenylalanine

<400> SEQUENCE: 1

Xaa Xaa Xaa Pro Trp Xaa
1               5

<210> SEQ ID NO 2
<211> LENGTH: 64
<212> TYPE: PRT
<213> ORGANISM: Mus musculus

<400> SEQUENCE: 2

Lys Asp Gln Glu Arg Glu Lys Arg Ser Ala Ser Asp Ser Asp Ser Asp
1               5                   10                  15

Glu Phe Pro Leu Arg Ile Pro Phe Pro Pro Tyr Gly Tyr Pro Phe Gly
                20                  25                  30

Thr Tyr Pro Pro Phe Leu Asn Gln Gly Tyr Pro Trp Tyr Tyr Tyr Tyr
            35                  40                  45

Tyr Pro Pro Phe Pro Leu Pro Phe Thr Pro Pro Pro Thr Ala Asp Pro
    50                  55                  60

<210> SEQ ID NO 3
<211> LENGTH: 61
<212> TYPE: PRT
<213> ORGANISM: Rattus norvegicus

<400> SEQUENCE: 3

Glu Asp Gln Glu Arg Glu Lys Arg Ser Ala Ser Asp Glu Leu Pro Glu
1               5                   10                  15

Arg Ile Ser Phe Pro Pro Phe Gly Pro Pro Phe Gly Gly Tyr Pro Pro
                20                  25                  30

Phe Phe Asn Gln Gly Asn Pro Trp Tyr Tyr Tyr Tyr Tyr Tyr Asn Pro
            35                  40                  45

Phe Leu Val Pro Ile Ile Pro Pro Thr Thr Arg Thr Pro
    50                  55                  60

<210> SEQ ID NO 4
<211> LENGTH: 64
<212> TYPE: PRT
<213> ORGANISM: Homo sapiens

<400> SEQUENCE: 4

Gln Asp Gln Glu Arg Glu Lys Arg Ser Ile Ser Asp Ser Asp Glu Leu
1               5                   10                  15
```

```
Ala Ser Gly Phe Phe Val Phe Pro Tyr Pro Tyr Pro Phe Arg Pro Leu
            20                  25                  30

Pro Pro Ile Pro Phe Pro Arg Phe Pro Trp Phe Arg Arg Asn Phe Pro
            35                  40                  45

Ile Pro Ile Pro Glu Ser Ala Pro Thr Thr Pro Leu Pro Ser Glu Lys
50                      55                  60

<210> SEQ ID NO 5
<211> LENGTH: 64
<212> TYPE: PRT
<213> ORGANISM: Pan troglodytes

<400> SEQUENCE: 5

Gln Asp Gln Glu Arg Glu Lys Arg Ser Ile Ser Asp Ser Asp Glu Leu
1               5                   10                  15

Ala Ser Gly Phe Phe Val Phe Pro Tyr Pro Tyr Pro Phe Arg Pro Leu
            20                  25                  30

Pro Pro Ile Pro Phe Pro Arg Phe Pro Trp Phe Arg Arg Asn Phe Pro
            35                  40                  45

Ile Pro Ile Pro Glu Ser Ala Pro Thr Thr Pro Leu Pro Ser Glu Lys
50                      55                  60

<210> SEQ ID NO 6
<211> LENGTH: 84
<212> TYPE: PRT
<213> ORGANISM: Mus musculus

<400> SEQUENCE: 6

Met Lys Thr Leu Leu Leu Ala Ala Ile Val Ala Val Thr Ala Cys
1               5                   10                  15

Leu Pro Val Pro Lys Asp Gln Glu Arg Glu Lys Arg Ser Ala Ser Asp
            20                  25                  30

Ser Asp Ser Asp Glu Phe Pro Leu Arg Ile Pro Phe Pro Pro Tyr Gly
            35                  40                  45

Tyr Pro Phe Gly Thr Tyr Pro Pro Phe Leu Asn Gln Gly Tyr Pro Trp
            50                  55                  60

Tyr Tyr Tyr Tyr Tyr Pro Pro Phe Pro Leu Pro Phe Thr Pro Pro Pro
65                  70                  75                  80

Thr Ala Asp Pro

<210> SEQ ID NO 7
<211> LENGTH: 81
<212> TYPE: PRT
<213> ORGANISM: Rattus norvegicus

<400> SEQUENCE: 7

Met Lys Ala Leu Leu Leu Ser Ala Ile Leu Ala Ile Thr Ala Cys
1               5                   10                  15

Leu Pro Val Pro Glu Asp Gln Glu Arg Glu Lys Arg Ser Ala Ser Asp
            20                  25                  30

Glu Leu Pro Glu Arg Ile Ser Phe Pro Pro Phe Gly Pro Pro Phe Gly
            35                  40                  45

Gly Tyr Pro Pro Phe Phe Asn Gln Gly Asn Pro Trp Tyr Tyr Tyr Tyr
            50                  55                  60

Tyr Tyr Asn Pro Phe Leu Val Pro Ile Ile Pro Pro Thr Thr Arg Thr
65                  70                  75                  80

Pro
```

<210> SEQ ID NO 8
<211> LENGTH: 85
<212> TYPE: PRT
<213> ORGANISM: Homo sapiens

<400> SEQUENCE: 8

```
Met Lys Lys Val Leu Leu Leu Ile Thr Ala Ile Leu Ala Val Ala Val
1               5                   10                  15

Gly Phe Pro Val Ser Gln Asp Gln Glu Arg Glu Lys Arg Ser Ile Ser
            20                  25                  30

Asp Ser Asp Glu Leu Ala Ser Gly Phe Phe Val Phe Pro Tyr Pro Tyr
        35                  40                  45

Pro Phe Arg Pro Leu Pro Pro Ile Pro Phe Pro Arg Phe Pro Trp Phe
    50                  55                  60

Arg Arg Asn Phe Pro Ile Pro Ile Pro Glu Ser Ala Pro Thr Thr Pro
65                  70                  75                  80

Leu Pro Ser Glu Lys
            85
```

<210> SEQ ID NO 9
<211> LENGTH: 85
<212> TYPE: PRT
<213> ORGANISM: Pan troglodytes

<400> SEQUENCE: 9

```
Met Lys Lys Val Leu Leu Leu Ile Thr Ala Ile Leu Ala Val Ala Ala
1               5                   10                  15

Gly Phe Pro Val Ser Gln Asp Gln Glu Arg Glu Lys Arg Ser Ile Ser
            20                  25                  30

Asp Ser Asp Glu Leu Ala Ser Gly Phe Phe Val Phe Pro Tyr Pro Tyr
        35                  40                  45

Pro Phe Arg Pro Leu Pro Pro Ile Pro Phe Pro Arg Phe Pro Trp Phe
    50                  55                  60

Arg Arg Asn Phe Pro Ile Pro Ile Pro Glu Ser Ala Pro Thr Thr Pro
65                  70                  75                  80

Leu Pro Ser Glu Lys
            85
```

<210> SEQ ID NO 10
<211> LENGTH: 443
<212> TYPE: DNA
<213> ORGANISM: Homo sapiens

<400> SEQUENCE: 10

```
atttctcata acagcgtcag agagaaagaa ctgactgaaa cgtttgagat gaagaaagtt      60
ctcctcctga tcacagccat cttggcagtg gctgttggtt tcccagtctc tcaagaccag     120
gaacgagaaa aaagaagtat cagtgacagc gatgaattag cttcagggtt ttttgtgttc     180
ccttacccat atccatttcg cccacttcca ccaattccat ttccaagatt tccatggttt     240
agacgtaatt ttcctattcc aatacctgaa tctgccccta caactcccct tcctagcgaa     300
aagtaaacaa gaaggaaaag tcacgataaa cctggtcacc tgaaattgaa attgagccac     360
ttccttgaag aatcaaaatt cctgttaata aagaaaaac aaatgtaatt gaaatagcac      420
acagcactct ctagtcaata tct                                             443
```

<210> SEQ ID NO 11

```
<211> LENGTH: 28
<212> TYPE: DNA
<213> ORGANISM: artificial
<220> FEATURE:
<223> OTHER INFORMATION: synthetic oligonucleotide primer

<400> SEQUENCE: 11
gggataaagt gataaaaacg aatagcca                                          28

<210> SEQ ID NO 12
<211> LENGTH: 25
<212> TYPE: DNA
<213> ORGANISM: artificial
<220> FEATURE:
<223> OTHER INFORMATION: synthetic oligonucleotide primer

<400> SEQUENCE: 12
acggaaatcc agaagatgca agcct                                             25

<210> SEQ ID NO 13
<211> LENGTH: 24
<212> TYPE: DNA
<213> ORGANISM: artificial
<220> FEATURE:
<223> OTHER INFORMATION: synthetic oligonucleotide primer

<400> SEQUENCE: 13
ggaggagtag aaggtggcgc gaag                                              24

<210> SEQ ID NO 14
<211> LENGTH: 17737
<212> TYPE: DNA
<213> ORGANISM: artificial
<220> FEATURE:
<223> OTHER INFORMATION: synthetic nucleotide sequence of a gene
      targeting construct

<400> SEQUENCE: 14
aaatggggct tggccatgat gtgtggttga tatacttagc gtcactccat tggacaaaac        60
tgattatccg ttgataacag cagttttggt tataaatagt ttcttgatta ggggtggaac       120
tttgtgtcca catcctcttc cctccatctt gggactttgt cttgtttgag taggaagttg       180
ggtgggtagg gaggtatttg agatctagaa gaagttgggc aaagggaaaa aatatgatga       240
aaatacattg tatgaaaaaa tgtaatggtg gtaaaggtac ccatgtggaa aaaaaaaag       300 aaaaagaaga aataaagta ggtagaagac ttgttgagaa ggatttcagt gggagagaga       360
atgaaagcag gcaacgaagg ctgaagtggt aaaaaaaata tcatcatata cacacagaaa       420
actataaaac gaaaaatgaa aaaatgtggt ggactcatgt gtgttggttg actgtccgtc       480
caacatcata gtgaattatg cagctggata aaaagaacct gtgcaccaga agatcttaga       540
taagccatgg tctcagagta gggactgatt acatacccta ctcattagaa gtgaggacaa       600
aagccatatg tggtcaagtg catacagtaa attcaagggg gaatcagaac acacaaggct       660
tctgaggaag gaggaggagg aggaggagga ggaggaggag gaggaggagg agaagaagga       720
ggaagtggag ttctgagaga atttttacat aacaggacaa tggatgggta ggtagggaga       780
atctggaagg agctagggga ggagagagaa tgtgatacaa atatattata tgaaaaaata       840
aaataattta agggaaccac aggaaagaaa taatagaact ttgttatttt aattaaaaaa       900
tcattattaa atgtcaagac ataaaatttc atgaagatag aaagtatatc tgggcctcaa       960
aaataagtga caactagcaa ttttttactag aatactttca gctaagtaaa agaaactaaa      1020
```

```
atcaactttt aggaaaggca ttcagaaaca tgccatacaa cacacacaca tacacgtatg    1080
ggtactcatg catacacaca cacacacaca cacacacaca catgcactta acaagtctac    1140
ctctgaatga gaacctactc ttacctcaga atgatcaaaa tgaaaactaa tatatgttga    1200
tatattgtat ttaacagatc atcagttcag ttctcttaaa gccagtgaaa caagaataaa    1260
tgttgttatg tataataaac tttagtgttt ctttggattt ctctacccct cgagtggcac    1320
tgtaaaatgc tggttataga tgggtcttgg aaaccaattg cagaaatcaa cataatattg    1380
acagaattct agttgtggta ttttaaatca agtgctaact ctctcaattt ctcaggccat    1440
tggcgtacac tggcgtaaga tctaataatc attttgcact tgctgctggc tgttctagag    1500
attaagtgga ataatagaca cgcaacactt ttgtctatag agcaataagc cccaaatcca    1560
tgagagacaa aatttaaagg aaaaccacaa aggaaatatt ctgtatcact caaccatagt    1620
ttctatgaaa ctaccagtat cactcatttc tcagtttcaa tggattatgg tagttgagtc    1680
agtagaatac tgactgatcc caggagcagc tttccagcca aggacttctc cattccattg    1740
tgctgggagt gtataaaaga gatgcaacag tgaggtgcct gtcatcttcc cctgacgata    1800
gcagtatcag ctagaaggag cagagtggag agtttcaggt aagaaggctc tgaactaatg    1860
ctgtaaacta tggatataca actcttctag gagacagatg gtatatgtac atattaattt    1920
tttcaaacta ccagaattga aactgtaatg ggacacttgc ttgaaattac aaacagtgat    1980
ttgactgtcc acttgtgtat ttctgtttgt ataaatttaa aaccaccatt tttctatagt    2040
aaggatttaa gaatgaccat aaaggaatct ttgcaaggac tgggcactga cgagaggaat    2100
ggaaatagca tcaggttcat aattttgaat tttatggacc aagtcaacaa atatggaagg    2160
aattctatgg gtatgaagaa ttaaccttcc atgcagtggt gcaaatcttt agtgacagca    2220
tttgggaggc aaggccagtg aatgtatctc tgtaagtttg aggccaacct cgtctatcca    2280
gtgagttcca ggacggccag agctacacag tgagtctctg tcttggccgg gaaaaaagaa    2340
ttaggacttt gttagtaaca tcctgttcat ctttaaagta tcatcattta tgcaccattc    2400
taatatgtca tattgatttc aaataataat tatttaaatt ctctttttata tcaacctttg    2460 aatgaaattg gtggtgccac aaaacacatc tgatgcataa acttttctt tttttaggtt    2520 ctctttcttt gcatgtttat tatttgtgta agaaaagtt actgatttgt gagagttgag    2580
tctgtatcat gctacattgc tgaatttgtt tatcatttct aaaagtttca cagtagaatt    2640
ttgggttctc ttatgtatgt aacaatatac tactagggct tgggggaaa acggtcattg    2700 gtaattatgg catatagcaa ttataaaaca aaggagtctg tgatgtgttt tctgtttaat    2760
gagattttaa ataatccttg aaaactattc ctttgtataa aattctctac aattctattc    2820
tcttcaagac ttatttcccc attctgtctc ttctatattc tctccatatt ttgtaacttc    2880
tgcccatagt atatatcaca tattgtttta cattacaaag acataattat ctatctctga    2940
gtagtctcca cctgaaaggg ctcaagcttt atagttatat ccttgagagt ggcctgcaca    3000
atgtctgaag aaggaaggta gaagtgtata aaatgaggga cacattgtac tatcggtttt    3060
ctatactgag agttggccat tagaatgcta aacctgacaa aacttttaaa tacatgtctt    3120
taaactcatc aattacatcc cagtatgctg tatattctag taacattttc attgatatga    3180
tgagaaagaa acaaagacag agttcaagat gtagcaacat tttattcttt tatgttttac    3240
tcttctgtct catagaaaag ggataaagtg ataaaaacga atagccatga tctcaaagtt    3300
gtccacaaat gatgttagtg aaatgggaaa tgagcatttt tctcagtgta aaataataaa    3360
tattcttcag aaaactgtag ttcatactga ccactaactc tctagttaat aaggctttta    3420
```

```
agacagtatt cataaatatg tgaatactta tttttaaaga actgatacaa tgaagtcata   3480
aaaacacaaa ccattccagt atttactttt gaaaagtttc ccactagtaa acaggcaata   3540
aactgcccct atgctactcc gtcataactt cgtatagcat acattatacg aagttatcgc   3600
tctcctgagt agggcccaaa tggccagcta agtcctgaga actattagtt acatacactg   3660
taccaggctt gcatcttctg gatttccgtt aataatcagt tttctttatg atgcctagaa   3720
caagatgaaa actcttctcc tgctcgctgc catcgtggca gtaactgctt gtctcccgt    3780 gagtactcac atctaatctc taaagtgttt atgaagttta gattcacgat tctcgacaat   3840
gttattgctc tttcttcaca ctttagtgtt taaagatact ttcaacctga cctgtagcat   3900
tatatttcag gaaatgtcat atgctctttg gtgcatgact gatgccacgt agttttgtg    3960 cagtagcaaa cacaataaca tttaaaaattc tctctgagaa atgggagcac catccagtac  4020
tagagcactt acctgatagc tgtctcagtt tctattgtcg tgataaacac cataaccaaa   4080
accagcttgg gggggttgt tttgttgcac tttgcagctt agctcttagg tcacatccca    4140
tcactaaagg atgccagagc agcaactaaa gacaggaaca ggagaccaga aacaaagctg   4200
aggctatgga gaggtgctgc ttgccgattt gctccctgtg gcttattcat catgcttcc    4260 catacaactt agggccacct gctcaaggat agtgctgact gagtggcctg ggtccttcca   4320
caccaataat taaagaagaa aatgcccctat agacttgccc aagagaaaac ggatggagac  4380
atcaggttcc ccttcccaga gaacccaact ttgtatctgg ttgacaaaaa caagcctgga   4440
cactaacttt gaggacccaa aggattctca aagtatcaaa ggatggttga tcctcagcac   4500 cacaaaaga aaaggcaatc atgatgacca gtagcatttt tcctgaata ttgcctctat     4560 atctggacaa ccaagtccta tattttgatg gatagcatga aacagtatta gaaagtagtt   4620
gaattatttt ttacatgtat atgcatatat ttctcatgtg tttacatcag gacgagttaa   4680
tttcacttat tgactttag gtgcctaagg accaggaacg agaaaaacga agtgtaagtt   4740
gcttttcatc ttcccatgtc agttttgttt gtgtgtgtgt gtctgtgtgt gtgtgtgtgt   4800
gtgtgtgtgt gtgtgtgtgt gtgtgtgtgt gtgtgtgtaa gatagtcaca actgtgatta   4860
aaggcattta gacacccaaa cctcttgacc tctgagagag tctcaaaaat ctttggaata   4920
ttagcattag actagtgtat agagtttgat ttcgggggaa tacctgaatt cagtataaat   4980
taattggtta atatctgcct atataaagaa aaaaacctt tcatttcata taaaagtgac   5040
atgcaggttt agttgtgtgt cactctgtga caaagggcac agtgcagttc tcacagggaa   5100
cttcctaaaa tacctcacct cttaaaggca acatttttca atagcattga gttagggacc   5160
aagtgatcta tctaagcata aatgatctaa gaacatttga cttcccattc caggtggtag   5220
taggccagtc ttaatgacaa aagtcggaaa aaaaaaaaca gcaaaacatt attttggtat   5280
gaacagacaa gtaaaaacat tcaagaaaaa tgggggcatg ggaatgaaga aaagacagac   5340
gtacttacag aaaaactggg atgaagtagg ccatgtgctc tgatgaaat gtacctgtgg    5400 cagcctcgaa attcatcact ctattatata cagcaggaat gagaaagaag tgagttagct   5460
aatgtcagca gaaggtctct ggatgggagt ggttttagat agcagtcatt tgggaggagg   5520
aagcaccaaa tgccgctttt gcacacactg gtttagcta actgtaacca tttcatacat    5580
tggctaggcg aagacttaaa cgttcttctg agcctaacct tgatttgcca ttcccttttgg  5640 tctaagacat tgaaatccctt gaccaggcca ttcttaggtc aataatattg cactccaccc  5700
atgcagcaca aaaactgata gaaatgtaga cacagaatga gaggaagaaa taagagatg    5760
```

-continued

```
attttcaaca tgtgatttgg ttaatggtca tatgaatcaa aacaatacat attacagagc    5820
cttcacctct cttatcattc gttgccttat agctatagaa agaattattt gaaaaatttg    5880
ctttgaagtc taagatttgg aatgtagtta tctctaattt tctaaactga ataattaag    5940
cccttgttaa tttacaaat aaagactggc ctttccttt atcaacaggc cagtgacagt    6000
gacagtgatg aattccctt acggattccc tttcccccat acgggtatcc atttggtaca    6060
tacccaccat tcttaaatca aggctacccg tggtattatt attattatcc tccttttccc    6120
ctgcccttca cccccctcc aactgcagat ccttaactgc aaatgaaaga aaagtcacac    6180
tgtggattat ttaaggtgag tttgaataat cagtcacttt ggctgttctg tttcttattt    6240
gtgagtataa acgcatcact ccatgaaaat gttacactgt tgctagctat taggatcgta    6300
catgttccg tggttttctg cagtaaatat tgttggtacc aacagtggag ttatatacta    6360
tgtgtccttt tgatccaata acacaacagt ttaaattcct tgtttgttac aatacaataa    6420
aaccaagtct gttttcataa tttatttaa gcattttcta ctaaaacagt tttccacttt    6480
gggatgaatc ataggaatag tagaagcaaa tgtcaatata aagctgagcc tgtatgaact    6540
tatgaatcta gacagtaaag gaaagtttaa gggttaggtt cttcctaacc cttaggaaag    6600
taagctaaga ttttttaatgt taatcaccca aaacaatggt gtatgcctaa cattaaaaaa    6660
aaaaaaccct atagccttat gtttcactta aaatatagtt actgttatct cagcatacca    6720
gactcaaagt ggtgagtctg caagccctgg atagattggg tacaggctat attgtagact    6780
aattacagac ccaaaacatt ttagaaaaca aaaacttctc actgtaatgc acatacatat    6840
aatatgtgta cacaaacaca tgcacacaca ctcatacatg cacatataca cacatgtaca    6900
cacatacaca catcataca tgcacacata catacataca tacatacata catacataca    6960
tgtacacaca cacagaaagg ctctgacttt ttctttttct attcagcatt catgtgctaa    7020
atgttttcca agtcttgagc tacatggatt tttatgacaa catatatcat aagatacaat    7080
atacgtgtat acgtataata acttcgtata gcatacatta tacgaagtta tggatcctga    7140
tatccctatg ctactccgtc gaagttccta ttctctagaa agtataggaa cttcattcta    7200
ccgggtaggg gaggcgcttt tcccaaggca gtctggagca tgcgctttag cagccccgct    7260
gggcacttgg cgctacacaa gtggcctctg gctcgcacac attccacatc caccggtagg    7320
cgccaaccgg ctccgttctt tggtggcccc ttcgcgccac cttctactcc tcccctagtc    7380
aggaagttcc ccccgcccc gcagctcgcg tcgtgcagga cgtgacaaat ggaagtagca    7440
cgtctcacta gtctcgtgca gatggacagc accgctgagc aatggaagcg ggtaggcctt    7500
tggggcagcg gccaatagca gctttgctcc ttcgctttct gggctcagag gctgggaagg    7560
ggtgggtccg ggggcgggct caggggcggg ctcaggggcg gggcgggcgc ccgaaggtcc    7620
tccggaggcc cggcattctg cacgcttcaa aagcgcacgt ctgccgcgct gttctcctct    7680
tcctcatctc cgggcctttc gacctgcagc ccggtggaca gcaagcgaac cggaattgcc    7740
agctggggcg ccctctggta aggttgggaa gccctgcaaa gtaaactgga tggctttctt    7800
gccgccaagg atctgatggc gcaggggatc aagatctgat caagagacag gatgaggatc    7860
gtttcgcatg attgaacaag atggattgca cgcaggttct ccggccgctt gggtggagag    7920
gctattcggc tatgactggg cacaacagac aatcggctgc tctgatgccg ccgtgttccg    7980
gctgtcagcg caggggcgcc cggttctttt tgtcaagacc gacctgtccg gtgccctgaa    8040
tgaactgcag gacgaggcag cgcggctatc gtggctggcc acgacgggcg ttccttgcgc    8100
agctgtgctc gacgttgtca ctgaagcggg aagggactgg ctgctattgg gcgaagtgcc    8160
```

```
ggggcaggat ctcctgtcat ctcaccttgc tcctgccgag aaagtatcca tcatggctga    8220
tgcaatgcgg cggctgcata cgcttgatcc ggctacctgc ccattcgacc accaagcgaa    8280
acatcgcatc gagcgagcac gtactcggat ggaagccggt cttgtcgatc aggatgatct    8340
ggacgaagag catcaggggc tcgcgccagc cgaactgttc gccaggctca aggcgcgcat    8400
gcccgacggc gaggatctcg tcgtgaccca tggcgatgcc tgcttgccga atatcatggt    8460
ggaaaatggc cgcttttctg gattcatcga ctgtggccgg ctgggtgtgg cggaccgcta    8520
tcaggacata gcgttggcta cccgtgatat tgctgaagag cttggcggcg aatgggctga    8580
ccgcttcctc gtgctttacg gtatcgccgc tcccgattcg cagcgcatcg ccttctatcg    8640
ccttcttgac gagttcttct gagcgggact ctggggttcg aaatgaccga ccaagcgacg    8700
cccaacctgc catcacgaga tttcgattcc accgccgcct tctatgaaag gttgggcttc    8760
ggaatcgttt tccgggacgc cggctggatg atcctccagc gcgggatct catgctggag     8820 ttcttcgccg tttccctgcc acagtctgag agctccctgg cgaattcggt accaataaaa    8880
gagctttatt ttcatgatct gtgtgttggt ttttgtgtgc ggcgcgccag cttggcgtga    8940
agttcctatt ctctagaaag tataggaact tccgctctcc tgagtaggtg catgtatatc    9000
ttgtaagttc tctagagaat gacccatttg gattagtaat catatacctt tcatttcttt    9060
caggttgctt tgaaattgaa tatgaaccac ttccttgaag gatcaatatt cctgttaaga    9120
gagaaaaata aaagcaattg aaatagcata tactgtggtc tcttcggaag tccttttact    9180
aagcatgaaa gggaagatcc tgagttttta tgttttatg actgttttta atttctcatt     9240
ttaaaaatgt aacatcttat taacttgggg gaactttata caagtataca atgcatgttg    9300
atgacattca tccttcccac cacgtcctca cttctcccag atctccatca cccaacattg    9360
tgtcctcttc attttttttt taatagccca ccaagtctaa gttgagttgc ccataaactt    9420
gtcgttattt ggccatccac gtaagccaca tccttaaaaa atgctgactc tcattctccc    9480
agaatccatc ttctcagtta tgggtgaagg cttgtgagcc ttccacttca tgctggaata    9540
tggggtgttt ccattgttgc aggacttatg caggcaacca gaactgcagt gggctcagga    9600
gtgtgtagtt ttatcatgtt gggaagattc tgtattgttc tagttttcct caatctctga    9660
ttcttacaat atttctatta cctcttctac tattgtccct gagccttgtg taaagaatag    9720
gagacttatg tcccatttgt ggctgagaac aatatatctt gtgaattttg accaattttc    9780
agtttctgct ctcaccaccc ataattcaca gaaacttctg cagtaaggtg tgagagctgc    9840
agtaatgtaa gagacagaga catggattta gaaagccact tgatacttag gccccttgtc    9900
agaataatat atttattata ataaaagtga acataaaat ttagcgtgtt ttaatataca     9960
tgtgtgaatt gtacacctag gtatgtgtct gtccatatcc tcatgtgcat atgtagaagc   10020
cggagttcaa cctcaaatat tccttcaggt tccacctact ttgtttttca agacatggtt   10080
tctcattggc ctgatgcttg ctgattaatc taggatggct gtccagtaag caccatggat   10140
ctctgtgtgt ctctgttttc ctcacattga gattagacat gcatgtcact gtacctgttt   10200
ttgatgtggc tttgttagtt ttggatatca aactcattgt ccgtaagctt acatgttatc   10260
tttgttactc ttctatgggt gtgaagagac accatgacta agacaattta taaaggaag    10320 tatttaatta ggggcttgct tacatcttca gagggtaaat cagaaattat gacatcaagc   10380
agttatgata ttggagaaat agctgagatt ttacatcttt ctgcacaagg cagaaagaca   10440
actgggaatg gtatcaactt ttaaacctca aacccaccc ccagtgatac ataccctcctc   10500
```

```
caacaagacc acactcccta atcctttcta aacagttcta taaattgcag aaacaagcat    10560
tcaaatatat gcacctatgg gggtcattct cattcaaaac ataacacatg gaaaccattt    10620
aatttgctaa gcttttggcc agccctaaat atacgtgatg gctcagcact ttagaaaaaa    10680
gcatgaagaa tagggggtgat tgagtcagca gtcctggtat atcttgaatg aaagtgtcca    10740
caggtttatg ttgtataaat gccttaatag taccaagaga gaaaattcac caaattaatc    10800
taaaatatat ttcaacaact gaatctgtac atactgcaga agagtaagct cgactcattg    10860
gaaaaggaca taaacaaaag aatatgttgt ctctaaaccc aaaagccagt aatagttaat    10920
atccttaaaa tagcattaaa atcattctta catgttacaa gaactttaaa aataaaagtc    10980
actacaaagt taaatctccc caaatctctt tcttgtctgg aaaaactgaa gatgaaagaa    11040
ttcctgagga ttttagatgc tcatagctcc agcacacggc agaaatgcaa aggtagatcc    11100
accggactcc tcggctttgg taacagtagc acttgcacaa aaataaattc tgagtcagga    11160
tcagagacta gttaaatcta tttcttttta ctttatgtca ggaagaaaaa tcatcttatg    11220
gcttttagga taatggatag ctgccactct ttctctggca ttacctcata gcaaaaattg    11280
aacatcattt ctgataggtc caataatcac tgaaagttcc ttatgttcgg cctcccaacc    11340
acaccacaca cacacacaca cacacacaca cacacacaca gacacacaaa gaggccctcg    11400
aggcccacca actaatccca agtttcgttt caaaatcttc tcccttcact tggctcccat    11460
atatcctaag ctcagaaaat ccaggcattg ccattgtctg caactaggct ttgtcacaca    11520
actatgcctt tgccatggtg atttctcctc gtgaaacata cagtcctcta attcagtatt    11580
catattcaat ttatctttta ataatcatgt tcaatattat gatcttcata aaaaatatct    11640
cagtcaaaaa aaaatgtcct cactatgacc tcctcccata gtactttatt tctgcgcttt    11700
ataagtctaa ccattctttg gtctttgttc ttcttgagtt tcatgtgttt tgcaaattgt    11760
atcttatatc ttgggtattc taagtttctg ggctaatatc cacttatagc tgacaccatt    11820
gcatacacta gcaagatttt gctgaaagga ccctgatata gctgtctctt gtgaggctat    11880
gctggggcct agcaaacaca gaagtggagg ctcatagtca gctatgatgg atcacagggc    11940
ccccaattga ggagctagag aaagtaccca aggagctaaa gggatctgca atcctatagg    12000
tggaacaaca atatgaacta accagtaccc cctggagctc gtgtctctag ctgcatatgt    12060
atgagaagac ggccatcagt ggaaagagag gcccattggt cttgcaaact ttatatgcct    12120
cagtacaggg gaactccagg gccaagaagt gggagtgggt gggtagggga gtgggtgggg    12180
ggagggtatt gtggacttttt gggatagcat tggaaatgta aatgaagaaa atacctaata    12240
ataataacaa tagtaacaat aataataata ataaaatgag tctaaccacg ctacagcttc    12300
tagtagaaca gtccatatca tttttctgcat cttacttaag ccttggaata tgacatcaat    12360
ctaaatgtac tccagtcctt agatgctcag tgactgctaa attgaatata ttaacaagaa    12420
ttaacaattc ctaatatttt taaaagagc attttcacac atatcaatgt ggaaggtggt    12480
aaaaggttca ttctctcagg aaatgaaatt attaaaatca gtatttaaat gttgacaaat    12540
ttattctatt caattacaat tttagggcag caagttgagt aatttcttgg ctatccattt    12600
tctgctgtag gaactctagt cataatcaag tcataaataa aattttgttc tgaatactac    12660
aattcataca tattgttata catgaattag acattcaaat ttctgaggat tttaatttat    12720
ctagtgttgt gtgggctttt tctagagcaa aattatataa aagacagtt tgtcctgttc    12780 actgtctctt cctactaacc tgatggtgaa cacagcgtaa tgccatgcag gaaggaaagg    12840
tacagaagtc atccaacaaa atctctgttg gacaatgagc ctttattatg tcacaatcgc    12900
```

```
tgcccttgtc tcggtggtaa attatcagga aattagaaaa gttctaagac tgtatctttc    12960
caccacaata aatttatgca cagatgagac cctttgcacc aaccatggaa acattgttct    13020
ctgtgtgcat cctggctgaa agtgaaggtc agcgtaatga ggcacttagc tatattggtg    13080
gacagaaact tctgtcttcc ttagtcattt gcagatatcg aattctaccg ggtaggggag    13140
gcgcttttcc aaggcagtct gagcatgcgc ttagcagccc cgctggcact tggcgctaca    13200
caagtggcct ytggcctcgc acacattcca catccaccgg taggcgccaa ccggctccgt    13260
tctttggtgg cccccttcgcg ccaccttctw ctcctcccct agtcaggaag ttcccccccg    13320
ccccgcagct cgcgtcgtsa ggacgtgaca aatggaagta gcacgtctca ctagtctcgt    13380
cagatggaca gcaccgctga gcaatggaag cgggtaggcc tttggggcag cggccaatag    13440
cagctttgct cctttcgcttt ctgggctcag aggctgggaa ggggtgggtc cggggcgggg    13500
ctcaggggcg ggctcagggg cggggcgggc gcccgaaggt cctccggagg cccggcattc    13560
tgcacgcttc aaaagcgcac gtctgccgcg ctgttctcct cttcctcatc tccgggcctt    13620
tcgacctgca ggtcctcgcc atggatcctg atgatgttgt tattcttcta atcttttgta    13680
tggaaaactt ttcttcgtac cacgggacta aacctggtta tgtagattcc attcaaaaag    13740
gtatacaaaa gccaaaatct ggtacacaag gaaattatga cgatgattgg aaagggtttt    13800
atagtaccga caataaatac gacgctgcgg gatactctgt agataatgaa acccgctct    13860 ctggaaaagc tggaggcgtg gtcaaagtga cgtatccagg actgacgaag gttctcgcac    13920
taaaagtgga taatgccgaa actattaaga aagagttagg tttaagtctc actgaaccgt    13980
tgatggagca agtcggaacg gaagagttta tcaaaaggtt cggtgatggt gcttcgcgtg    14040
tagtgctcag ccttcccttc gctgagggga gttctagcgt tgaatatatt aataactggg    14100
aacaggcgaa agcgttaagc gtagaacttg agattaattt tgaaacccgt ggaaaacgtg    14160
gccaagatgc gatgtatgag tatatggctc aagcctgtgc aggaaatcgt gtcaggcgat    14220
ctctttgtga aggaacctta cttctgtggt gtgacataat tggacaaact acctacagag    14280
atttaaagct ctaaggtaaa tataaaattt ttaagtgtat aatgtgttaa actactgatt    14340
ctaattgttt gtgtatttta gattccaacc tatgaactg atgaatggga gcagtggtgg    14400
aatgcagatc ctagagctcg ctgatcagcc tcgactgtgc cttctagttg ccagccatct    14460
gttgtttgcc cctcccccgt gccttccttg accctggaag gtgccactcc cactgtcctt    14520
tcctaataaa atgaggaaat tgcatcgcat tgtctgagta ggtgtcattc tattctgggg    14580
ggtggggtgg ggcaggacag caagggggag gattgggaag acaatagcag gcatgctggg    14640
gatgcggtgg gctctatggc ttctgaggcg gaaagaacca gctggggctc gacctcgagg    14700 gggggcccgta tacccagctt tgttcccctt tagtgagggt taattgcgcg cttggcgtaa    14760
tcatggtcat agctgtttcc tgtgtgaaat tgttatccgc tcacaattcc acacaacata    14820
cgagccggaa gcataaagtg taaagcctgg ggtgcctaat gagtgagcta actcacatta    14880
attgcgttgc gctcactgcc cgctttccag tcgggaaacc tgtcgtgcca gctgcattaa    14940
tgaatcggcc aacgcgcggg gagaggcggt ttgcgtattg ggcgctcttc cgcttcctcg    15000
ctcactgact cgctgcgctc ggtcgttcgg ctgcggcgag cggtatcagc tcactcaaag    15060
gcggtaatac ggttatccac agaatcaggg gataacgcag gaaagaacat gtgagcaaaa    15120
ggccagcaaa aggccaggaa ccgtaaaaag gccgcgttgc tggcgttttt ccataggctc    15180
cgcccccctg acgagcatca caaaaatcga cgctcaagtc agaggtggcg aaacccgaca    15240
```

```
ggactataaa gataccaggc gtttccccct ggaagctccc tcgtgcgctc tcctgttccg   15300
accctgccgc ttaccggata cctgtccgcc tttctccctt cgggaagcgt ggcgctttct   15360
catagctcac gctgtaggta tctcagttcg gtgtaggtcg ttcgctccaa gctgggctgt   15420
gtgcacgaac cccccgttca gcccgaccgc tgcgccttat ccgtaactat cgtcttgag    15480
tccaacccgg taagacacga cttatcgcca ctggcagcag ccactggtaa caggattagc   15540
agagcgaggt atgtaggcgg tgctacagag ttcttgaagt ggtggcctaa ctacggctac   15600
actagaagga cagtatttgg tatctgcgct ctgctgaagc cagttacctt cggaaaaaga   15660
gttggtagct cttgatccgg caaacaaacc accgctggta gcggtggttt ttttgtttgc   15720
aagcagcaga ttacgcgcag aaaaaaagga tctcaagaag atcctttgat cttttctacg   15780
gggtctgacg ctcagtggaa cgaaaactca cgttaaggga ttttggtcat gagattatca   15840
aaaggatct tcacctagat ccttttaaat taaaaatgaa gttttaaatc aatctaaagt   15900
atatatgagt aaacttggtc tgacagttac caatgcttaa tcagtgaggc acctatctca   15960
gcgatctgtc tatttcgttc atccatagtt gcctgactcc ccgtcgtgta gataactacg   16020
atacgggagg gcttaccatc tggccccagt gctgcaatga taccgcgaga cccacgctca   16080
ccggctccag atttatcagc aataaaccag ccagccggaa gggccgagcg cagaagtggt   16140
cctgcaactt tatccgcctc catccagtct attaattgtt gccgggaagc tagagtaagt   16200
agttcgccag ttaatagttt gcgcaacgtt gttgccattg ctacaggcat cgtggtgtca   16260
cgctcgtcgt ttggtatggc ttcattcagc tccggttccc aacgatcaag gcgagttaca   16320
tgatccccca tgttgtgcaa aaaagcggtt agctccttcg gtcctccgat cgttgtcaga   16380
agtaagttgg ccgcagtgtt atcactcatg gttatggcag cactgcataa ttctcttact   16440
gtcatgccat ccgtaagatg cttttctgtg actggtgagt actcaaccaa gtcattctga   16500
gaatagtgta tgcggcgacc gagttgctct tgcccggcgt caatacggga taataccgcg   16560
ccacatagca gaactttaaa agtgctcatc attggaaaac gttcttcggg gcgaaaactc   16620
tcaaggatct taccgctgtt gagatccagt tcgatgtaac ccactcgtgc acccaactga   16680
tcttcagcat cttttacttt caccagcgtt tctgggtgag caaaaacagg aaggcaaaat   16740
gccgcaaaaa agggaataag ggcgacacgg aaatgttgaa tactcatact cttcctttt    16800
caatattatt gaagcattta tcagggttat tgtctcatga gcggatacat atttgaatgt   16860
atttagaaaa ataaacaaat aggggttccg cgcacatttc cccgaaaagt gccacctaaa   16920
ttgtaagcgt taatattttg ttaaaattcg cgttaaattt ttgttaaatc agctcatttt   16980
ttaaccaata ggccgaaatc ggcaaaatcc cttataaatc aaaagaatag accgagatag   17040
ggttgagtgt tgttccagtt tggaacaaga gtccactatt aaagaacgtg gactccaacg   17100
tcaaagggcg aaaaaccgtc tatcagggcg atggcccact acgtgaacca tcaccctaat   17160
caagtttttt ggggtcgagg tgccgtaaag cactaaatcg gaaccctaaa gggagccccc   17220
gatttagagc ttgacgggga agccggcga acgtggcgag aaaggaaggg aagaaagcga   17280
aaggagcggg cgctagggcg ctggcaagtg tagcggtcac gctgcgcgta accaccacac   17340
ccgccgcgct taatgcgccg ctacaggcgc gtcccattc gccattcagg ctgcgcaact   17400
gttgggaagg gcgatcggtg cgggcctctt cgctattacg ccagctggcg aaggggggat   17460
gtgctgcaag gcgattaagt tgggtaacgc cagggttttc ccagtcacga cgttgtaaaa   17520
cgacggccag tgagcgcgcg taatacgact cactataggg cggccgctac ttggagaact   17580
actggcaatt attaatgtct gagggaagtg atactttttt ctccagttgg gtagctggtg   17640
```

```
attaatttct catgactggt gaattacttg caaacaactc taaactcagt gagtcatcca    17700
aaaagaaggc tattttatgt caatcagata ttccagc                             17737
```